(12) United States Patent
Chow et al.

(10) Patent No.: US 7,803,523 B2
(45) Date of Patent: Sep. 28, 2010

(54) WHOLE BLOOD PREPARATION FOR CYTOMETRIC ANALYSIS OF CELL SIGNALING PATHWAYS

(75) Inventors: Sue Chow, Markham (CA); David Hedley, Toronto (CA); T. Vincent Shankey, Miami, FL (US); Patricia Grom, Coral Springs, FL (US)

(73) Assignees: University Health Network, Toronto (CA); Beckman Coulter, Inc., Fullerton, CA (US)

( * ) Notice: Subject to any disclaimer, the term of this patent is extended or adjusted under 35 U.S.C. 154(b) by 1035 days.

(21) Appl. No.: 10/928,570

(22) Filed: Aug. 27, 2004

(65) Prior Publication Data

US 2006/0046272 A1 Mar. 2, 2006

(51) Int. Cl.
*A01N 1/02* (2006.01)
*G01N 1/00* (2006.01)

(52) U.S. Cl. .................. 435/2; 435/7.21; 435/7.23; 435/7.24; 435/7.25; 435/40.5; 436/521; 436/522; 436/546; 436/17; 436/18; 436/166; 436/174; 436/175; 436/176; 436/177

(58) Field of Classification Search .................. 435/1.3, 435/2, 7.21, 7.23, 7.24, 7.25, 7.92, 40.5, 435/286.5, 286.7, 288.3; 436/522, 286.7, 436/546, 10, 17, 18, 63, 64, 164, 166, 175–177, 436/521, 174
See application file for complete search history.

(56) References Cited

U.S. PATENT DOCUMENTS

| 4,801,549 | A |   | 1/1989 | Cremins et al. |
| 5,422,277 | A | * | 6/1995 | Connelly et al. ............... 436/10 |
| 5,496,734 | A | * | 3/1996 | Sakata .......................... 436/63 |
| 5,597,688 | A | * | 1/1997 | Connelly et al. ............... 435/5 |
| 5,804,387 | A |   | 9/1998 | Cormack et al. |
| 5,968,738 | A |   | 10/1999 | Anderson et al. |
| 6,534,279 | B1 |  | 3/2003 | Agthoven et al. |
| 6,821,789 | B2 |  | 11/2004 | Augello et al. |
| 7,326,577 | B2 | * | 2/2008 | Shults et al. ................ 436/176 |
| 7,354,773 | B2 | * | 4/2008 | Rubio et al. ................. 436/177 |
| 2005/0084924 | A1 | * | 4/2005 | Shults et al. ............... 435/40.5 |
| 2006/0141549 | A1 | * | 6/2006 | Mahajan et al. ................ 435/15 |

FOREIGN PATENT DOCUMENTS

| EP | 0 743 519 A2 | 11/1996 |
| EP | 0 971 233 A1 | 1/2000 |

OTHER PUBLICATIONS

Chow et al., Measurement of MAP Kinase Activation by Flow Cytometry Using Phospho-Specific Antibodies to MEK and ERK: Potential for Pharmacodynamic Monitoring of Signal Transduction Inhibitors, Cytometry: Communications in Clinical Cytometry 45: 72-78 (2001).*

Francis et al., Rapid Single-Step Method for Flow Cytometric Detection of Surface and Intracellular Antigens Using Whole Blood, Cytometry 25: 58-70 (1996).*

Drevs, et al., "Receptor Tyrosine Kinases: The Main Targets for New Anticancer Therapy", Curr Drug Targets, 4:113-21 (2003).

Fjallskog, et al., "Expression of Molecular Targets for Tyrosine Kinase Receptor Antagonists in Malignant Endocrine Pancreatic Tumors", Clin Cancer Res, 9:1469-73 (2003).

Tashiro, et al., Overexpression of Cyclin D1 contributes to Malignancy by Up-Regulation of Fibroblast Growth Factor Receptor 1 via the pRB/E2F Pathway, Cancer Res, 63:424-31 (2003).

Kmet, et al., "A Review of p53 Expression and Mutation in Human Benign, Low Malignant Potential, and Invasive Epithelial Ovarian Tumors", Cancer, 97:389-404 (2003).

Petit, et al., "Assessment of fluorochromes for cellular structure and function studies by flow cytometry", Biol Cell, 78:1-13 (1993).

Mullins, J. Michael, "Overview of Fluorophores", Methods Mol Biol, 34:107-16 (1994).

Shapiro, Howard M., "Optical Measurements in Cytometry: Light Scattering, Extinction, Absorption, and Fluorescence", Methods Cell Biol, 63:107-29 (2001).

Loken, et al., "Establishing Optimal Lymphocyte Gates for Immunophenotyping by Flow Cytometry", Cytometry, 11:453-459 (1990).

Chow, et al., "Measurement of MAP Kinase Activation by Flow Cytometry Using Phospho-Specific Antibodies to MEK and ERK: Potential for Pharmacodynamic Monitoring of Signal Transduction Inhibitors", Cytometry, 46:72-78 (2001).

Bland, et al., "Statistical Methods for Assessing Agreement Between Two Methods of Clinical Measurement", Lancet, 1:307-31 (1986).

(Continued)

*Primary Examiner*—Gailene R Gabel
(74) *Attorney, Agent, or Firm*—Holly O. Soehnge; Mitchell E. Alter

(57) ABSTRACT

This invention is directed to a method for preparation of a biological sample for measurement of protein epitopes that allows for the preservation of intracellular protein epitopes and detection of signal transduction pathways based on the ability to capture transient activation states of the epitopes. The method provided by the invention allows for the rapid fixation of biological samples containing red blood cells, to ensure that epitopes of signal transduction molecules and other intracellular protein epitopes are preserved in the active state. The method of the invention further allows for lysis of red blood cells, thereby making it a useful method for cytometric analysis of biological samples, including, for example, whole blood, bone marrow aspirates, peritoneal fluids, and other red blood cell containing samples. The invention also provides a method to recover or "unmask" epitopes on intracellular antigens that have been made inaccessible by the cross linking fixative necessary to fix the sample. Significantly, the methods of the invention allow preservation and analysis of phospho-epitope levels in biological samples taken directly from patients to determine disease-specific characteristics.

37 Claims, 15 Drawing Sheets

OTHER PUBLICATIONS

Riley, John, "Statistical Analysis and Optimal Classification of Blood Cell Populations Using Gaussian Distributions", Ph.D. dissertation: Florida International University (2003), Chapter 5, pp. 43-56, "Fisher Distances and Applicatoins to Measures of Similarity".

Supplementary European Search Report for the European Patent Appl. No. EP 05785535, EPO, mailed Mar. 3, 2008.

Shafaie, Atousa et al., "A Robust Whole Blood Preparation for Absolute Counting," *Cytometry*, Supplement, No. 10, p. 145, (2000).

Chow, S. et al., "Whole Blood Fixation and Permeabilization Protocol with Red Blood Cell Lysis for Flow Cytometry of Intracellular Phosphorylated Epitopes in Leukocyte Subpopulations," *Cytometry*, vol. 67, No. 1, pp. 4-17, (2005).

\* cited by examiner

Calculation of Fisher Distance

Distance = $\sqrt{X^2 + Y^2}$

Fisher Distance = $\dfrac{Distance}{SD(A) + SD(B)}$

WHOLE BLOOD PREPARATION FOR CYTOMETRIC ANALYSIS OF CELL SIGNALING PATHWAYS

FIELD OF THE INVENTION

This invention relates generally to the field of sample preparation for cytometry and, more specifically, to methods capable of biological sample preparation for signal transduction measurements by flow cytometry and image cytometry.

BACKGROUND OF THE INVENTION

Flow cytometry has become an indispensable tool in clinical and basic immunological research due to its ability to distinguish subsets in heterogeneous populations of cells. Recently, major advances have been made in both flow cytometry instrumentation and applications, expanding the number of possible simultaneous analysis parameters to thirteen or more. With more parameters available, researchers have begun to identify more well-defined and biologically interesting subsets of lymphocytes samples based upon surface epitope staining.

Flow cytometry is routinely used for the identification of cellular populations based on a surface phenotype and also used for cellular based assays such as cytotoxicity, viability, and apoptosis, among others. It is well understood that flow cytometry offers the capability to assess the heterogeneity of cellular subsets that exist in complex populations such as peripheral blood. Although surface staining may be an effective means of characterizing cells, it does not provide information about the functional responses of those cells to stimuli that are immediately reflective of intracellular events. Even in cases where the marker used is a cytokine receptor or receptor tyrosine kinase, levels of the antigen do not always correlate with cellular response to the specific ligand. Therefore, methods have been developed to characterize cells by measuring levels of intracellular epitopes: cytokines, DNA, mRNA, enzymes, hormone receptors, cell cycle proteins, and of phosphorylated signaling molecules. As a result, research applications of flow cytometry are being increasingly applied to the measurement of intracellular proteins that regulate cell processes and represent important therapeutic targets for novel anticancer agents.

Current proteomic approaches, such as 2-dimensional SDS-PAGE and Mass-Spectroscopy of protein post-translational modifications are extremely powerful and have provided valuable insights into many intracellular activation processes. However, as the cells are lysed, it is obvious that the readout of these experiments is an average for protein activation states across the cell population(s). Significant biological events can be masked by such averaging, as there is no provision for the collection of information on the distribution of protein activation in individual cells within a population nor is there the ability to retroactively identify the cellular populations that corresponded to the detectable levels of active proteins. Therefore significant information on immune cell population variations that exist in both defined cellular populations and across different cell subtypes is undetectable and cannot be addressed by methodologies that require cell lysis for protein analysis. Ultimately, protein activation signaling cascades must be measured in their biological context to be both relevant and free of artifact.

Of particular interest has been the recent development of techniques for the analysis of signal transduction pathways, based on the use of phosphorylation state-specific antibodies. Multiparameter flow cytometric analysis allows for small subpopulations—representing different cellular subsets, differentiation or activation states—to be discerned using cell surface markers. As such, the usage of single cell techniques to characterize signaling events provides the ability to perform multiparametric experiments to identify the distinct signaling junctures of particular molecules in defined lymphocyte populations and to obtain a global understanding of the extent of signaling networks by correlating several active kinases involved in signaling cascades simultaneously, at the single cell level. Furthermore, the incorporation of these methods into conventional clinical flow cytometry protocols will have far-reaching application for the classification of hematological malignancies including the selection of patients for highly specific molecular cancer therapeutics, and for monitoring drug effects in patients.

Analysis of signal transduction pathways by flow cytometry presents technical problems that are not currently encountered in routine clinical applications. The phosphorylation states of individual signaling elements are rapidly modified in response to specific kinases and phosphatases, and therefore subject to artifactual changes during sample storage and preparation. Cellular responses to activating or inhibitory inputs are likely to be more informative than steady state measurements of phosphorylation states. Many anticancer agents show reversible binding to their molecular target. As a result, pharmacodynamic monitoring has to measure whole blood samples rather than isolated leukocytes. Ultimately, the existing and potential applications of phospho-specific flow cytometry to clinical settings, including characterization of immune system development and signaling, antigen-specific T-cell responses, drug screening, and disease phenotyping, must take into account that phosphorylation is a transient, reversible event that is indicative of the activation status of signaling proteins.

Thus, there exists a need to develop methods capable of biological sample preparation for signal transduction measurements by flow cytometry that are robust and suitable for general clinical application and able to capture the phosphorylation events that represent the activation status of signaling proteins. The present invention satisfies this need and provides related advantages as well.

SUMMARY OF THE INVENTION

This invention is directed to a method for preparation of a biological sample for measurement of protein epitopes that allows for the preservation of intracellular protein epitopes and detection of signal transduction pathways based on the ability to capture transient activation states of the epitopes. The method provided by the invention allows for the rapid fixation of biological samples containing red blood cells, to ensure that epitopes of signal transduction molecules and other intracellular protein epitopes are preserved in the active state. The method of the invention further allows for lysis of red blood cells, thereby making it a useful method for cytometric analysis of biological samples, including, for example, whole blood, bone marrow aspirates, peritoneal fluids, and other red blood cell containing samples. The invention also provides a method to recover or "unmask" epitopes on intracellular antigens that have been made inaccessible by the cross linking fixative necessary to fix the sample. Significantly, the methods of the invention allow preservation and analysis of phospho-epitope levels in biological samples taken directly from patients to determine disease-specific characteristics.

DETAILED DESCRIPTION OF THE INVENTION

Figure 1:
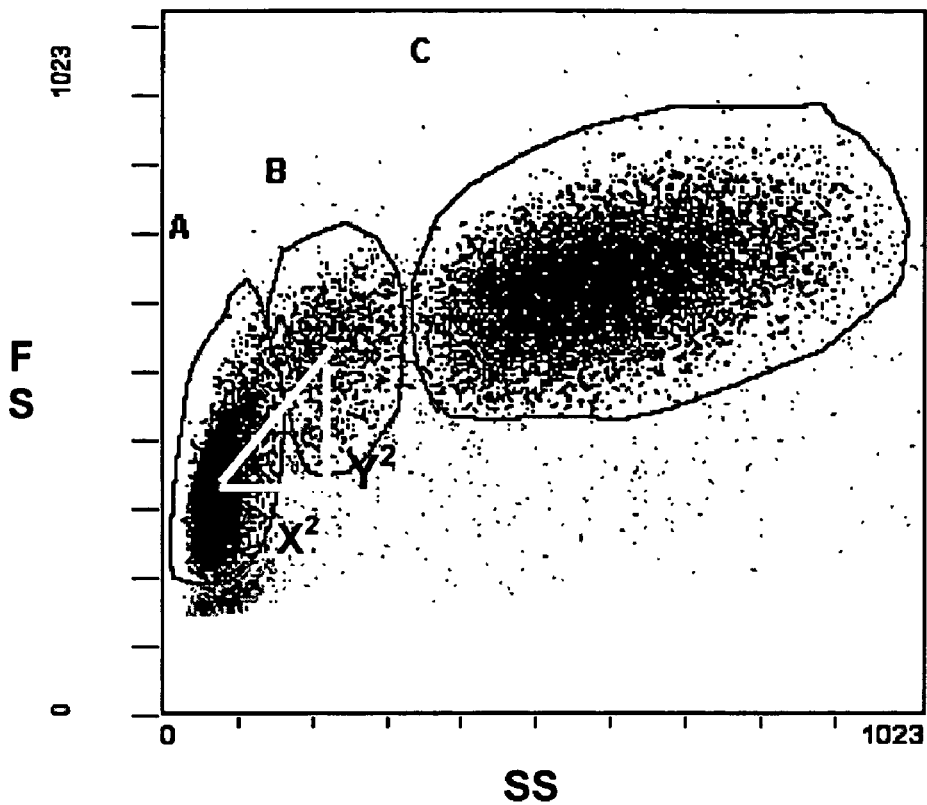
FIG. 1 provides an illustration of the technique used to calculate Fisher Distances for WBC populations using light scatter measurements from whole blood samples measured by flow cytometry.

This invention is directed to a method for preparation of a biological sample for measurement of protein epitopes that allows for the preservation of intracellular protein epitopes and detection of signal transduction pathways based on the ability to capture transient activation states of the epitopes. The method provided by the invention allows for the rapid fixation of biological samples containing red blood cells, to ensure that epitopes of signal transduction molecules and other intracellular protein epitopes are preserved in the active state. The method of the invention further allows for lysis of red blood cells, thereby making it a useful method for cytometric analysis of biological samples, including, for example, whole blood, bone marrow aspirates, peritoneal fluids, and other red blood cell containing samples. The invention also provides a method to recover or "unmask" epitopes on intracellular antigens that have been made inaccessible by the cross linking fixative necessary to fix the sample. Significantly, the methods of the invention allow preservation and analysis of phospho-epitope levels in biological samples taken directly from patients to determine disease-specific characteristics.

The methods provided by the invention are based, in part, on the discovery that use of whole blood samples to study signal transduction pathways using cytometric analysis can be accomplished by an initial fixation step that accomplishes preservation of the activation state of cellular epitopes without rendering red blood cells insensitive to subsequent lysis. This discovery overcomes the problem encountered in traditional methods that remove red blood cells from the sample by density gradient separation or lysis prior to fixation and, due to the processing time that delays fixation, can result in de-phosphorylation of signal transduction epitopes. In contrast, by providing a method for rapid fixation of a biological sample containing red blood cells that allows the elimination of a time consuming separation or lysis step that delays fixation, the methods of the invention allow the user to capture and measure protein epitopes in their active state.

In particular embodiments, the present invention provides a method for whole blood fixation, permeabilization and red blood cell lysis that rapidly fixes cells as an initial step, preserves light scatter measurements, maintains key cell surface epitopes used to identify specific hematologic cell populations, and provides optimal phospho-epitope measurements.

The methods of the invention are aimed at preparing a biological sample for measurement of cellular epitopes by cytometry. An advantage of cytometry is the ability to differentiate cell types based on their surface staining properties, for example, CD3 for T cells, CD 19 for B cells. While the methods of the invention allow for preservation of intracellular epitopes for detection, the important goal of maintaining surface epitope recognition necessary to differentiate cell types also can be accomplished via the invention methods.

Thus, the methods describe herein allow the user to preserve the physical integrity of both surface and intracellular epitopes for cytometric detection.

The methods provided by the invention are further partly based on the discovery that the detection of particular target epitopes, for example, phospho-specific epitopes, including p-ERK, p-STAT1, p-STAT5, can be optimized with an alcohol step.

In one embodiment, the invention provides a method for preparing a red blood cell containing biological sample for measurement of protein epitopes that preserves intracellular protein epitopes for subsequent detection. The method encompasses a fixation step that includes contacting said sample with a fixative in an amount to achieve a final concentration sufficient to crosslink proteins, lipids and nucleic acid molecules; a detergent step that encompasses addition of a detergent to the biological sample in an amount to achieve a final concentration sufficient to lyse the red blood cells and permeabilize the white blood cells; and a labeling step, wherein the sample is contacted with a detectable binding agent specific for a one or more epitopes.

In one embodiment, the invention provides a method for preparing a red blood cell containing biological sample for measurement of protein epitopes that preserves intracellular protein epitopes for subsequent detection. The method encompasses a fixation step that includes contacting the sample with a fixative in an amount to achieve a final concentration sufficient to crosslink proteins, lipids and nucleic acid molecules. The fixative concentration can be between approximately 0.1 percent and approximately twenty percent, between approximately 0.5 percent and approximately 15 percent; between approximately 1 percent and approximately 10 percent, between approximately 1 percent and approximately 8 percent, between approximately 1 percent and approximately 4 percent, between approximately 1 percent and approximately 2 percent. The fixative can be added either in concentrated solution or in diluted form to achieve the desired concentration. The fixative can be any appropriate agent desired by the user, for example, formaldehyde or paraformaldehyde, or formalin.

The method of the invention for preparing a red blood cell containing biological sample for measurement of protein epitopes that preserves intracellular protein epitopes for subsequent detection further encompasses a detergent step, wherein detergent is added in an amount to achieve a final concentration sufficient to lyse red blood cells and permeabilize white blood cells. The detergent concentration can be selected by the user based on a variety of conditions and can be in a range of between approximately 0.1 percent and approximately 8 percent; between approximately 0.1 percent and approximately 7 percent; between approximately 0.1 percent and approximately 6 percent; between approximately 0.1 percent and approximately 5 percent; between approximately 0.1 percent and approximately 4 percent; between approximately 0.1 percent and approximately 3 percent; between approximately 0.1 percent and approximately 2 percent; between approximately 0.1 percent and approximately 1 percent.

The detergent can be selected based on a variety of factors and can be an ionic or a non-ionic detergent. Detergents are preferably selected from among non-ionic detergents. One currently preferred detergent is ethyoxylated octylphenol, which is referred to by the commercial name of Triton® X-100 (Sigma T9284, polyethylene glycol p-(1,1,3,3-tetramethylbutyl)-phenyl ether). In preferred embodiments, the methods are practiced with Triton® X-100. Suitable detergents for the invention methods can permeabilize cells and retain surface epitope integrity. Ionic detergent useful in the invention further include octylphenoxypoly(ethyleneoxy) ethanol, commercially available as Igepal™. CA-630 (Sigma N-6507) or Nonidet® P-40 (NP-40, octylphenolpoly (ethyl-eneglycolether))(Sigma), Brij-58® (poly(oxvethylene) cetyl ether), and linear alcohol alkoxylates, commercially available as Plurafac™ A-38 (BASF Corp) or Plurafac™ A-39 (BASF Corp).

In complex cell populations such as, for example, undiluted peripheral blood, bone marrow aspirate and peritoneal fluid, it can be useful to distinguish cell subsets by surface markers and detect intracellular phospho-epitope staining in one procedure. The methods provided by the present invention for preparing a red blood cell containing biological sample for measurement of protein epitopes that preserves intracellular protein epitopes for subsequent detection are amenable to be used for combining intracellular epitope detection with detection of cell surface epitopes. In the method provided by the invention, both intracellular and extracellular epitopes can remain intact so as to allow subsequent measurement by cytometric analysis. For example, the surface detection of typical T cell markers including, for example, CD4, CD3, CD62L, and CD8, can be combined with intracellular epitope detection.

In a further embodiment, the invention the method encompasses a further alcohol step that encompasses contacting the biological sample with alcohol in an amount to achieve a final concentration sufficient to unmask cellular epitopes that are lost due to cross-linking during the fixation step. As described herein, the alcohol step can preserve the majority of extracellular epitopes and can be adjusted by the user in length of incubation, temperature and concentration depending on the epitopes to be preserved.

It is understood in the art that for clinical applications involving multiparameter cytometric analysis, it is desirable to unmask and preserve for detection a subset of extracellular epitopes associated with particular biological markers that can include, for example, CD3, CD35, HLA DR, CD4, HLA DP, HLA DQ, CD5, CD10, CD11a, CD29, CD32, CD36, CD38, CD40, CD45, CD49, CD54, CD55, CD56, CD58, CD59, CD71, CD83, CD85i(ILT2), CD85j(ILT3), CD85f (ILT-4), CD86, CD87, CD99, CD103, CD116, CD126 CD135, CD206, CD208(DC-LAMP), b2-Microglobulin, cBcl2, CCR5, CXCR4, HLA ABC, L25, MPO, CD3, CD79, and surface CD2, CD4, CD8, CD11b, CD13, CD14, CD15, CD16, CD19, CD20, CD21, CD23, CD24, CD25, CD28, CD33, CD34, CD35, CD41, CD42b, CD61, CD62L, CD64, CD65, CD66b, CD69, CD72, CD94, CD106, CD122, CD138, CD154, CD158a, CD161, NKb1 and others known in the art that can be selected based on the intent of the user.

The skilled person will be able to select a final alcohol concentration based on other variables including, for example, incubation time, temperature and particular epitopes targeted for unmasking and measurement. The final alcohol concentration can be between approximately 25 percent and approximately 75 percent, between approximately 30 percent and approximately 70 percent, between approximately 35 percent and approximately 65 percent, between approximately 40 percent and approximately 60 percent, between approximately 45 percent and approximately 55 percent. The alcohol can further be selected from the group consisting of ethanol and methanol. If desired, acetone can be substituted for alcohol in the alcohol step. The sample can be contacted with alcohol or acetone at a temperature, for example, approximately −30 degrees Celsius, approximately −20 degrees Celsius, approximately −10 degrees Celsius, approximately −5 degrees Celsius, approximately 0 degrees Celsius, approximately 4 degrees Celsius, approximately 6 degrees Celsius, approximately 8 degrees Celsius, or any other temperature that facilitates the unmasking of intracellular epitopes without reducing the reactivity of cell surface epitopes.

If desired, a biological sample prepared by a method of the invention can be stored following the alcohol step at temperatures below freezing point, for example, at approximately −40 degrees Celsius, at approximately −30 degrees Celsius, at approximately −20 degrees Celsius, at approximately −10 degrees Celsius, at approximately −5 degrees Celsius, and can retain the light scatter characteristics and integrity of extracellular epitopes, without diminishing the accessibility or changing the activation state of intracellular epitopes for periods of up to two months. It is understood, that the percentage of loss of signal is related to a variety of factors including, for example, the percent remaining water and the target epitope. In a preferred embodiment, the sample can be stored at approximately −20 degrees Celsius for two or more, three or more, five or more, 10 or more, 12 or more, 14 or more, 16 or more, 20 or more days, 30 or more days, 40 or more days, 50 or more days, 60 or more days. The stability of phospho-epitopes in alcohol can vary based on a variety of factors understood in the art, for example, the percentage of water remaining in the sample and the target epitope. Thus, the invention method provides for stability of phospho-epitopes in alcohol and allows long term storage of biological samples for several days up to 2-3 weeks or longer prior to analysis.

In various embodiments of the invention, a red blood cell containing biological sample is prepared for measurement of epitopes that can include, for example, viral particles, immunoglobulins, estrogen receptors, cytokines, and specific intracellular proteins. It is understood that the staining of static protein molecules can provide insight into cellular responses to stimuli in long-term experiments. The methods of the invention allow for correlation of extracellular markers with intracellular signaling events, or signaling events with one another, can produce insights into immune cell roles and the intricacies of signaling that are impossible to observe without monitoring events simultaneously in single cells.

Although exemplified herein with regard to intracellular phospho-epitopes, the methods of the invention are equally applicable for preparation of biological samples aimed at measuring other post-translational modifications including, for example, ubiquitination, glycosylation, methylation, acetylation, palmitolyation, or protein-protein interactions. Thus, the invention enables the detection of non-phospho epitopes of a variety of proteins within cells, expanding the utility of the methods further. Labeled binding agents can be selected by the user based on the particular cellular events to be studied. The methods provided by the invention allow for the examination of pathways in detailed time courses and pathway-specific manners that have previously not been available. Although diverse intracellular epitopes can be selected for flow cytometric analysis, it is understood that the user can optimize and tailor the method provided herein for the specific epitope in question by taking into account factors including, for example, localization, conformation/structure, accessibility by antibodies, and stability of the epitope. The methods provided herein are generally applicable to multicolor, multiparameter cytometry analysis.

Phosphorylation is a transient, reversible event indicative of the activation status of signaling proteins. Therefore, by measuring the phosphorylation state of proteins by flow cytometry, one can determine which signaling cascades are used in response to specific stimuli such as cytokines or growth factors, the kinetics of signaling, and the downstream targets that are transcribed. In addition, comparing diseased cells to healthy samples can easily identify aberrant signaling events, a trait that is useful for phenotyping cancers and immune disorders. Thus, in diagnostic settings, the methods of the invention can be used to prepare a biological sample for diagnostic flow cytometric assays of pathologic human samples based on, for example, phospho-protein status. In additional applications, the methods of the invention can be used to prepare a biological sample for screening of primary cell populations against molecular libraries to discover novel inhibitors and activators of kinase signaling cascades.

The methods of the invention for preparing a red blood cell containing biological sample for measurement of protein epitopes while preserving intracellular protein epitopes for subsequent detection are further useful in applications directed to immune system characterization including, for example, immune cell development by monitoring phospho-signature of developing T, B, or other lineage specific cells to correlate intracellular activities with stages of cellular differentiation; immune disease state profiling including combining tetramer staining with intracellular signal assessment to study antigen-specific T cells in viral and/or bacterial infections with the potential to monitor lymphocyte subsets for responses under acute and chronic infections; monitoring lymphocyte populations in disease murine models or patients, such as blood borne leukemias or autoimmune diseases such a rheumatoid arthritis to correlate phospho-signatures with disease manifestation; biochemical signatures of rare cell populations including dendritic cells, naive and memory effector cells, stem cells, that cannot be analyzed by conventional biochemical techniques; multidimensional assessment of cell signaling networks to understand cell function; identification of signaling thresholds and connections between disparate signaling cascades; monitoring of virally infected cells for altered function and intracellular signaling; and characterizing immune cell response patterns to cytokines and extracellular stimuli.

The methods of the invention for preparing a red blood cell containing biological sample for measurement of protein epitopes while preserving intracellular protein epitopes for subsequent detection are further useful in applications directed to pharmacodynamic monitoring and drug screening including, for example, intracellular kinase screens for rapid identification of specific inhibitors/modulators of target kinases; drug screening in primary cells to determine subset-specific efficacy and side effects; target validation of compound specificity by analyzing multiple intracellular pathways simultaneously; clinical trials by monitoring particular compounds for their effects during drug treatment on cellular populations of interest; identification of phospho-epitopes on kinases as diagnostic indicators of disease progression by correlating intracellular biochemical differences with additional clinical parameters; and phospho-epitope analysis during vaccination protocols to monitor efficacy at the cellular level.

As described above, the methods of the invention have utility to prepare biological samples for pharmacodynamic profiling. For example, phospho-specific flow cytometry can be used to profile disease states via their signaling status and response to particular compounds. Correlation of a phospho-epitope signature to the progression of a disease can be used in the development of therapies tailored to individual patients that are in early or late stages of a disease. For example, various tyrosine kinase receptors including Flt-3, PDGF-R, EGF-R and HER2, have been correlated with disease severity and prognosis in leukemias and breast cancer and are targets of drug therapy (Drevs et al., *Curr Drug Targets* 4:113-21, 2003; Fjallskog et al., *Clin Cancer Res* 9:1469-73, 2003). It is also known in the art that several intracellular molecules are indicators of actively dividing cancers such as p53 and cyclin proteins as described by Tashiro et al., *Cancer Res* 63 424-31, 2003, and Kmet et al., *Cancer* 97: 389-404, 2003. While cDNA microarrays and protein arrays provide information about abundance of molecules, these assays do not provide information about active states. Proteins that are present in low concentrations can play large roles in disease progression if they are constitutively active, a trait that can only be characterized by phospho-specific analysis. Thus, the methods provided by the invention for preparation of a red blood cell containing biological sample that preserve intracellular protein epitopes for detection confer upon the user the ability to correlate levels of proteins with their activity in particular disease states.

As described herein, the methods provided by the invention have utility in a variety of clinical settings including, for example, the detection of tumor masses, analysis of biopsies and tissue-derived samples based on the ability to prepare a red blood cell containing biological sample for cytometric analysis. By allowing the user to profile aberrant signaling, and subsequently analyze the efficacy and specificity of therapies both before and during clinical trials, the methods have expanded utility in the study and therapy of cancer and immune system diseases. As more phospho-epitope specific antibodies are developed and validated for flow cytometry, biological samples can be screened to find possible leads for drug development and further research into the causes of particular diseases. Based on their applicability to red blood containing biological samples, including undiluted peripheral blood, the methods of the invention allow preservation and analysis of phospho-epitope levels in biological samples taken directly from patients to determine disease-specific characteristics.

The methods provided by the invention also have utility in clinical settings including, for example, monitoring an individual patient's responsiveness to molecularly targeted therapies—for example, in Chronic Myelogenous Leukemia (CML); monitoring the ability of Gleevec™ to inhibit phosphorylation of STAT5 in whole blood or bone marrow samples as a marker of the drug's in vivo activity to predict loss of drug effect commonly seen in CML patients before it becomes clinically apparent); in AML (Acute Myelogenous Leukemia) for monitoring inhibitors of Flt-3 by monitoring downstream pathways, including STAT, MAPK and PKB/AKT); in Multiple Myeloma (MM) monitoring newly developed molecularly targeted inhibitors by monitoring MARK, PI3K, STAT, and Wnt pathways.

The methods provided by the invention also have utility in monitoring the effect of multiple drug combination therapies on specific types of tumors. For example, as it is known that most CML patients will eventually fail monotherapy with Gleevec™, most institutions are requiring multimodal therapies. The methods provided herein can be used to monitor the in vitro effect of Gleevec™ in combination with other agents, for example flavopiridol or cytarabin, by monitoring of downstream signal transduction pathways, such as MAPK, STATs, apoptosis, to help select combinations with potential efficacy in vivo. The methods provided herein can be used to study signal transduction pathways in individual patients with AML and MM. In this embodiment, blood or bone marrow samples can be treated with specific pathway stimuli and/or inhibitors, for example, Flt-3 ligand, PMA and Steele factor =/−UO-126 (MAPK inhibitor), Rapamycin (mTOR inhibitor) for AML, and subsequently measuring base-line, inducible and inhibitable levels of phosphorylated (activated) key proteins in multiple pathways in conjunction with cell surface markers.

As described herein, in preferred embodiments, the invention methods can be used to prepare a red blood cell containing biological sample for measurement of protein epitopes so as to allow preservation of intracellular phospho-epitopes for detection, including, for example, ERK, p38, JNK, and signal transducer and activator of transcription 3 (STAT3), STAT1, STAT5, STAT6, AKT/PKB, mTOR, S6 Kinase, Histone proteins (e.g. Histone H3), ATM, NFkappaB, GSK3, and others. Thus, the method provided by the invention allows for preservation of intracellular phospho-epitopes that are involved in signal transduction pathways. The methods provided by the invention for preparing a red blood cell containing biological samples achieve preservation of intracellular phospho-epitopes for detection, in part, through a rapid cell fixation step that effectively "freezes" the phosphorylation status of proteins. Furthermore, the lysis and permeabilization steps, which can be combined in a single step or performed separately, provide access for the detectable binding agents to their cognate epitopes, which must be preserved in the permeabilized target cells in the proper natured or denatured conformation. It is understood in the art that signaling cascades are often driven by protein phosphorylation on downstream effectors that activate the effectors to carry out their roles. Thus, phospho-specific labeled binding agents, for example, antibodies can be useful to recognize these active proteins and distinguish the "on-off" state of signaling events.

Cascades that utilize phosphorylation as a means of activating downstream effectors are well known in the art. Multiple signaling cascades can be measured simultaneously, for example, through the use of different fluorophore labels to determine specificity of ligands or inhibitors and can included, for example, the mitogen activated protein (MAP) kinase cascade and the Janus kinase-signal transducer and activator of transcription (Jak-Stat) pathway. The MAP kinases, extracellular regulated kinase (ERK), c-Jun N-terminal kinase (JNK), and p38, are doubly phosphorylated (on Thr and Tyr residues), then translocate into the nucleus to phosphorylate various transcription factors. STAT proteins are activated by growth factors and cytokines such as IFN-g, IL-4, and GM-CSF. Upon phosphorylation by Jaks, STAT proteins dimerize and enter the nucleus where they bind to DNA directly to modulate transcription. Thus, the invention methods for preparing a red blood cell containing biological sample for measurement of protein epitopes while preserving intracellular protein epitopes for subsequent detection are useful in applications directed at measuring dynamic signaling events that occur rapidly after cell stimulation or stress.

In the mitogen activated protein (MAP) kinase cascade, signaling begins at the cell surface and is passed from a MAP kinase kinase kinase (MEKK) to a MAP kinase kinase (MEK) to a MAP kinase and finally to a transcription factor. Each member of this cascade is activated by phosphorylation by the upstream member. Phosphorylation of transcription factors often increases DNA binding affinity or alters their conformation to cause dimerization and DNA binding. In the JAK-Stat cascade, dimerization of cytokine receptors leads to the activation of JAKs which then phosphorylate STATs in their dimerization domains leading to dimerized STATs entering the nucleus and activating transcription. Phosphorylation also can provide docking sites for other proteins to bind and localize to specific intracellular locations, such as phosphorylation of tyrosine motifs on receptor tyrosine kinases. While usually resulting in "positive" activity, phosphorylation events can also effect negative results, as for the T cell protein Lck, where phosphorylation inhibits enzymatic activity, and it is a dephosphorylation event by a phosphatase that causes Lck to signal.

To measure phosphorylation events uniquely, labeled binding partners specific to the phosphorylated form of a protein can be raised. This is typically done by using short phosphorylated peptide immunogens coupled to carrier proteins. Thus, detectable binding agents specific for different phospho-residues within the same signaling protein can be utilized in the methods provided by the invention, such that subsequent measurement provides insight into residues important for particular signaling events. Phospho-specificity can be confirmed by comparing resting versus stimulated cells, treating samples with phosphatases prior to analysis, competing with phosphorylated peptides versus non-phosphorylated ones, and normalizing phospho-protein levels to total protein content.

The method provided by the invention encompasses a labeling step, wherein the biological sample is contacted with a detectable binding agent specific for one or more epitopes. In order to subsequently measure the presence of one or more epitopes in the biological sample via cytometry, a binding agent can be a monoclonal antibody, polyclonal antisera that is adsorbed and/or affinity purified or otherwise enriched in antibodies specific for the one or more target epitopes, as well as an antibody fragment such as an enzymatically produced monovalent (Fab) or bivalent (F(ab'$_2$) antigen binding fragment. In addition, a binding agent can be an antibody-like molecule or mimetic.

In the labeling step, also commonly referred to in the art as a staining step, the sample is contacted with a saturating amount of labeled binding agent, preferably a fluorophore-conjugated antibody, which will bind to those cells which express the epitope. The cells expressing the epitope are then identified by the signature fluorescent signal emitted by the fluorophore when excited by laser light of the proper wavelength. Preferred fluorophores include the phycobiliproteins B-phycoerythrin (B-PE), R-phycoerythrin (R-PE) and allophycocyanin (APC), which are suitable for applications that require either high sensitivity or simultaneous multicolor detection. If desired, tandem conjugates containing two labels, for example, a phycoerythrin-labeled binding reagent in combination with a green-fluorescent detection reagent, can be used to detect two different signals using simultaneous excitation with the spectral line of the instrument laser. If desired, activity-based labels can be designed and synthesized that consist, for example, of alpha-bromobenzylphosphonate as a phosphatase-specific trapping device and a linker that connects the trapping device with a biotin tag for visualization and purification as described by Kumar et al., *Proc. Natl. Acad. Sci., USA* 101:7943-48, (2004).

Phospho-specific antibodies can be conjugated to a fluorophore to create primarily labeled antibodies that are detectable binding agents suitable for practicing of the methods provided by the invention. When choosing a fluorophore label for conjugation the fluorophore label's absorbance spectrum must match the laser line used in the cytometer and its emission must fall within detection filter sets. In addition, the label cannot interfere with the binding agent, for example, antibody binding characteristics or permeability through the cell structure. It is understood that large protein fluorophores like PE or APC may slow antibody entry into cells and affect its binding characteristics. Small molecule labels, for example, fluorophores such as FITC, Alexa 488, and Alexa 647 can provide the best staining characteristics providing proper control of fluorophore-to-protein ratios. Extensive discussion of fluorophore uses and applications in flow cytometry can be found in Petit et al., *Biol. Cell* 78:1-13, 1993; Mullins, Methods Mol Biol 34: 107-16 (1994); and Shapiro, *Methods Cell Biol* 63:107-29, 2001.

Flow cytometry devices and protocols are well known in the art, and have been amply described in numerous publications. See, e.g., *Flow Cytometry and Sorting*, 2$^{nd}$ ed. (1990) M. R. Melamed et al., eds. Wiley-Liss; *Flow Cytometry and Cell Sorting*, 2$^{nd}$ ed. (2000) A. Radbruch, Springer-Verlag; and *In Living Color: Protocols in Flow Cytometry and Cell Sorting* (2000) Diamond and Demaggio, eds, Springer-Verlag. Flow cytometry methods are also described in U.S. Pat. Nos. 5,968,738 and 5,804,387; the disclosures of which are herein incorporated by reference.

The invention thus provides a method for preparing a red blood cell containing biological sample for measurement of protein epitopes that allows for the preservation of intracellular protein epitopes for detection by cytometry, for example, flow cytometry or laser scanning cytometry. Cytometry is an extremely powerful multi-parameter method for analyzing phospho-specific and other non-phospho epitopes and has various advantages over analysis by methods such as Western blotting or ELISA. To maintain accuracy and semi-quantitative results, the cytometric detection can be validated by comparison to traditional methods such as Western blotting and ELISAs.

Cytometry allows analysis of B cells versus T cells, diseased/cancerous cells versus healthy cells, cells in one stage of development versus those in another stage, without any prior cell sorting or depletion. By enabling preparation of biological samples in a manner that preserves intracellular epitopes for detection, the methods of the invention allow for immediate comparisons between cell types. It is understood that several signaling cascades or members of one particular cascade can be analyzed simultaneously based on the detectable agents selected. In embodiments aimed at detection of multiple epitopes, a flow cytometer that is capable of multi-color analyses, for example, 2, 4, 6, 8, or more different colors, can be used. Thus, the method enables profiling of diseases based on their signaling states or by comparing their response to stimuli to normal, healthy cells. In this regard, neoplastic disorders are frequently characterized by overexpressed or constitutively active signaling molecules. The methods of the invention have further applicability for preparation of a biological sample for cell-based drug screening with flow cytometry, which can encompass simultaneous monitoring of several signaling cascades to determine drug specificity.

Detection by cytometry allows the user to analyse rare subsets of cells within complex populations. By allowing analysis of rare cell subsets in heterogeneous populations, flow cytometry can be used to monitor signaling events in environments that best simulate those in vivo, in particular, in the presence of many cell types. As described herein, the method of the invention allows preparation of red blood cell-containing biological samples that freezes signaling events at nearly any time point for later staining.

It is understood, that the methods of the invention can be performed in parallel on many samples, for example, in a 96 well plate format, to rapidly measure intracellular signaling events. In various embodiments, a biological sample such as undiluted peripheral blood, bone marrow aspirate or peritoneal fluid can be stimulated with a variety of cytokines and measured for phosphorylation of MAP kinases such as ERK, p38, and JNK or STAT transcription factors in several different cell types, for example, T cells, B cells, and NK cells. Thus, with phospho-specific flow cytometric methods, only one particular subset of lymphocytes, for example, B cells or T cells, can be targeted based on response to a stimulus not exhibited by other sub-populations. The ability to distinguish between cell subpopulations and detect cell types present in a sample individually can clarify changes that would appear small and may be undetectable if viewed in context of the whole population.

The methods provided by the invention can encompass one or more incubation steps, for example, between the fixation step and detergent step as well as between the detergent step and subsequent labeling step. It is envisioned that an incubation step for a time period ranging between approximately 30 seconds and approximately one hour follows the contacting of the biological sample with the fixative agent. It is contemplated that a second incubation step follows the contacting of the sample with detergent and precedes the labeling step and lasts for a time period ranging between approximately 30 seconds and approximately one hour. In a presently preferred embodiment, the time period for the second incubation step is approximately 10 minutes.

The method of the invention can further encompass one or more centrifugation steps. As exemplified herein, a first centrifugation step aimed at removal of detergent can be performed prior to the labeling step. In addition, a further centrifugation step can be performed after the alcohol step to remove the alcohol. It is understood that washing steps and resuspension in appropriate buffer, for example, phosphate buffered saline (PBS), can be performed at various steps as desired by the user.

As described herein, the invention provides methods that encompass the addition of fixative prior to the removal (lysis) of red blood cells and the permeabilization of target white blood cells. As a result the methods provided by the invention allow access to intracellular or intranuclear compartments by labeled binding agents, for example, antibodies, fragments thereof or antibody-like molecules. In addition, the invention provides embodiments of the method that include an alcohol step as described herein, that provides a means to "unmask" protein epitopes made inaccessible by fixation, a step shown to be necessary for the detection of phosphorylation on key signal transduction proteins, such as ERK 1,2.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. As used herein the singular forms "a", "and", and "the" include plural referents unless the context clearly dictates otherwise.

It is understood that modifications which do not substantially affect the activity of the various embodiments of this invention are also included within the definition of the invention provided herein. Accordingly, the following examples are intended to illustrate but not limit the present invention.

EXAMPLE I

Red Blood Cell Lysis, Fixation and Permeabilization of Whole Blood Samples

This example describes and compares preparation of whole blood samples by hypotonic lysis followed by fixation and detergent lysis subsequent to fixation.

Briefly, Phorbol myristate acetate (PMA, Sigma Chemical Corp., St. Louis, Mo.) was prepared as a 40 M working solution in 100% anhydrous ethanol and used in whole blood at a final concentration of 400 nM. Triton® X-100 (polyethylene glycol p-(1,1,3,3-tetramethylbutyl)-phenyl ether) and other detergents used in the examples were purchased as the Surfact-Pak™ Detergent Sampler kit from Pierce Biotechnology (Rockford, Ill.). The Sampler kit contains seven different non-ionic detergents (Tween®-20, Tween®-80, Triton® X-100, Triton® X-114, Nonidet® P-40, Brij-35® and Brij-58®, all supplied as 10% solutions in water), and three powders (nonionic Octyl-B-Glucoside, and Octyl-B-Thioglucopyaranoside, and zwitterionic CHAPS). Powdered detergents were dissolved in PBS (Ca++ and Mg++ free) to make 10% solutions. All detergents were diluted immediately before use in PBS.

For intracellular staining of phospho-specific epitopes, fixed and permeabilized cells (with or without methanol treatment) were washed once with cold wash buffer and centrifuged. To the cell pellet, antibodies (single or multiple antibodies) diluted in wash buffer were added to give a final volume of 100 ρl and incubated at 40 C for 15-30 minutes. A monoclonal antibody to phospho-ERK1/2 (Thr 202/Tyr 204, clone E10) was used (Cell Signaling Technologies, Beverly, Mass.), and was conjugated with Alexa Fluor™ 488 (Molecular Probes, Eugene, Oreg.) according to the manufacturers directions. Conjugated phospho-ERK1/2 had a dye to protein ration between 4.3 and 6.3, and was used at an optimal antibody concentration (0.2 µg conjugated phospho-ERK1/2 per $10^6$ cells in 100 µl) determined by prior antibody titration experiments. Anti-Tubulin (FITC conjugate, clone TB1A337.7) was obtained from Beckman Coulter, Inc. and used at a concentration of 0.5 µg per $10^6$ cells in 100 µl. After antibody staining, samples were resuspended in 2 ml wash buffer, and filtered through 35 micron nylon mesh (Small Parts, someplace in PA), centrifuged, and resuspended in 150 to 300 µl wash buffer prior to analysis using a Beckman Coulter Epics® Elite™ flow cytometer.

For cell surface plus intracellular staining, whole blood samples (100 µl) were processed for staining with selected monoclonal antibodies following Q-Prep™ treatment per manufacturers instructions (Beckman Coulter, Inc., Miami, Fla.), or Method B, either with, or without treatment with 50% cold methanol. Monoclonal anti-CD antibodies (added after cell sample preparation using Method B or B') included CD45 (clone J0.33), CD3 (clone UCHT-1), CD19 (clone J4.119), CD 13 (clone SJ/D1), CD14 (clone RMD52), and CD33 (clone D3HL60.251). All anti-CD-antibodies were obtained from Beckman Coulter, Inc. (Miami, Fla.) and were used as PE conjugates at antibody concentrations recommended by the manufacturer. Following antibody incubation for 30 min at room temperature, tubes were centrifuged (645X G for 4 min), resuspended in 1 ml wash buffer, and immediately analyzed using either an FC-500™, or Epics XL™ flow cytometers (Beckman Coulter, Inc., Miami, Fla.).

For experiments measuring changes in phospho-specific epitopes, flow cytometric measurements were performed using an Epics Elite™ flow cytometer (Beckman Coulter, Inc.) equipped with an air-cooled argon laser using 20 mW 488 nm illumination. FITC or Alexa Fluor™ 488 fluorescence was collected through a 525+/−10 nm bandpass filter, and PE was collected through a 575+/−10 nm bandpass filter, with minimal compensation used to eliminate FITC or Alexa Fluor™ 488 signal in the PE channel. Two to ten thousand positive events (generally CD3 positive) were acquired and saved in list mode files. Data analysis was performed using Epics Elite™ software, calculating mean fluorescence intensity (MFI) and percent positive events.

In experiments comparing the relative resolution of lymphocytes, monocytes and granulocytes using FALS and side scatter measurements, and experiments measuring the relative fluorescence intensity of selected surface markers in whole blood samples prepared using the three different techniques (Q-Prep™, Formaldehyde/Triton (without alcohol) [Method B], or Formaldehyde/Triton with alcohol [Method B']), either an FC-500™ or Epics XL™ flow cytometer (Beckman Coulter, Inc.) was used in the standard configuration provided by the manufacturer. Illumination was provided using 488 nm (only) and instrument settings for the PE channel (575+/−10 nm) were maintained at identical values, counting a total of 45,000 cells for each measurement. A FALS discriminator was used, set to eliminate the majority of platelets and small debris.

Quantitative differences in the recovery of light scatter populations (lymphocytes, monocytes and granulocytes) following Q-Prep™, Method B, or Method B plus 50% MeOH treatment (indicated as Method B') were determined by comparing the results of CBC analysis with the flow cytometry based light scatter determined populations. Verification of light scatter-based populations was performed using simultaneous measurements of CD45 (FITC) versus side-scatter as described by Loken et al., *Cytometry* 11:453-459,1990.

Figure 2:
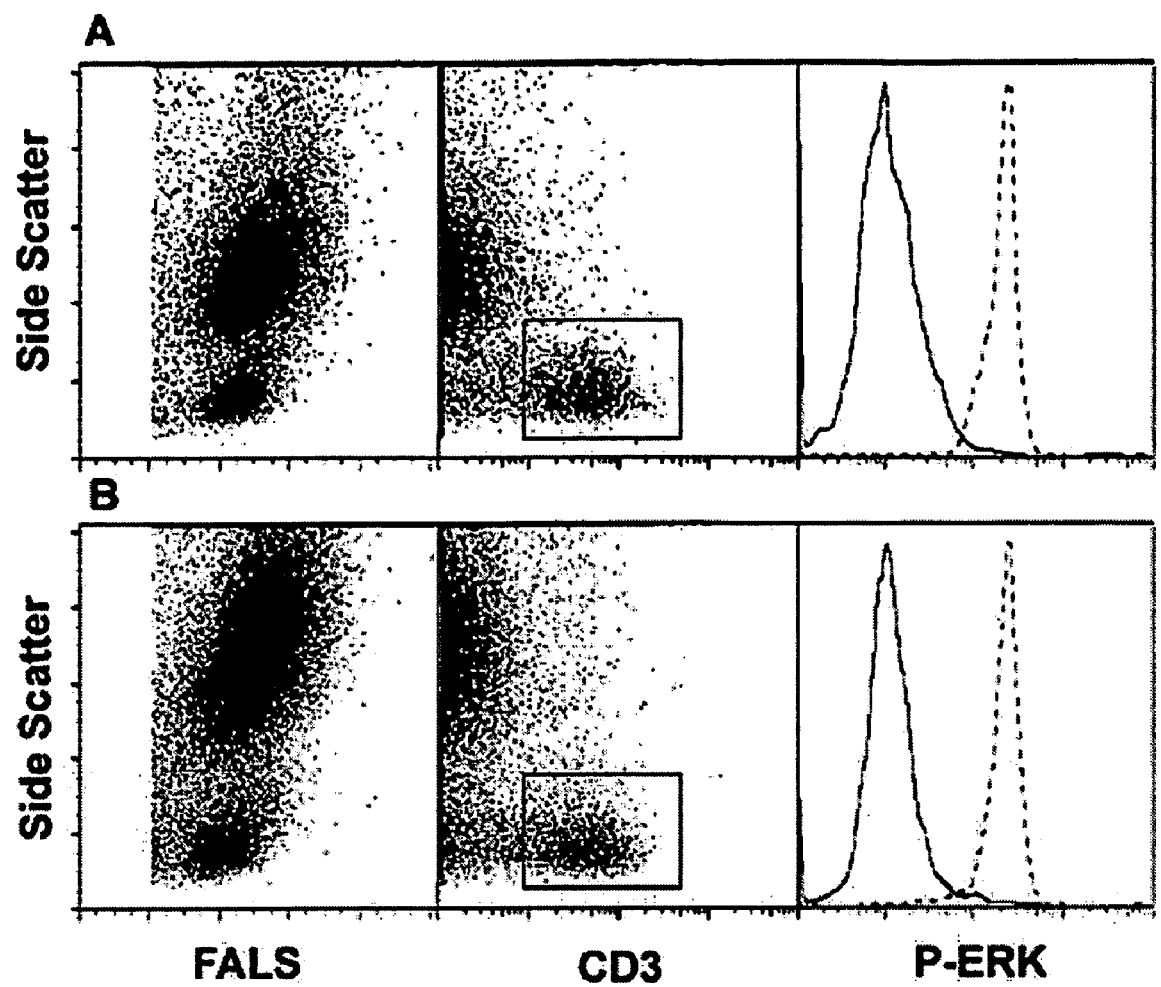
FIG. 2 shows the impact of hypotonic lysis without (top panels) or with fixation (bottom panels) immediately after whole blood activation. In the modified Method A (bottom panels) the sample was fixed immediately after hypotonic lysis of RBC's. Both methods show similar signal to noise (S/N) for phospho-ERK. The immediate fixation method generally provides better resolution of light scatter populations, but lower percentages of CD3-positive T-cells.

As shown in FIG. 2, the hypotonic lysis technique (Method A) routinely gave a 20-25 fold increased signal for phospho-ERK1/2, comparing PMA stimulated to unstimulated whole blood. The level of phospho-specific ERK on CD3 positive peripheral blood lymphocytes is measured in order to target the measurement to lymphocytes as described by Chow et al., *Cytometry* 46:72-78, 2001. This was done, in part, due to the poor resolution of white blood cell populations by light scatter following the hypotonic lysis technique (FIG. 2, left panels). No significant differences were observed in the phospho-ERK signal (ratio of PMA stimulated versus unstimulated samples) using Method A (FIG. 2 top panels) compared with the modified hypotonic lysis technique employing formalin fixation immediately after RBC lysis (FIG. 2, lower panels). These results demonstrate that a delay in the fixation of whole blood samples has no significant impact on the measured levels of phospho-ERK.

Based on the technical difficulties associated with the hypotonic RBC lysis technique, detergent lysis followed by fixation was undertaken. Increasing concentration of crosslinking fixative, time of incubation, or increasing temperature are factors that make red blood cells more resistant to detergent lysis. A series of experiments was performed to screen different detergents to evaluate their ability to lyse red blood cells, following cross linking fixation. For these experiments, 100 ul whole blood was fixed with 35 ul 10% formaldehyde (final concentration 2%) for 10 min at RT. Fixed whole blood samples were then treated with one of three different concentrations (0.001, 0.01, and 0.1%) of each detergent at room temperature (without removal of fixative), and monitored visually to detect red blood cell lysis for periods of up to 2 hours.

Figure 3:
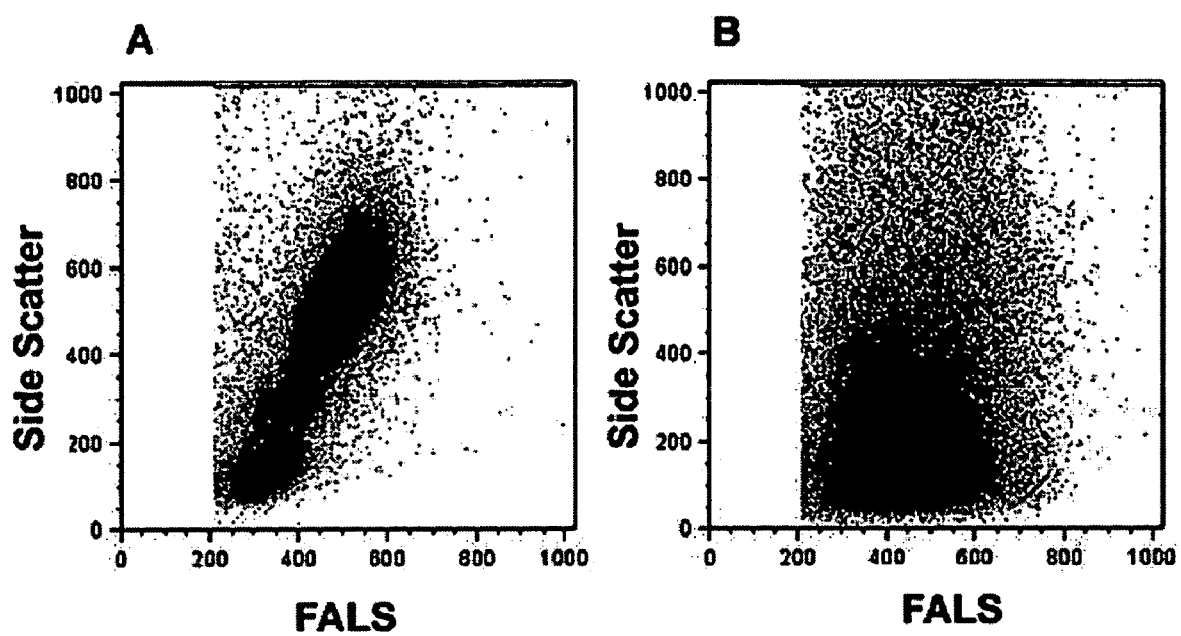
FIG. 3 shows the impact of different detergents on light scatter measurements of whole blood. Treatment of fixed whole blood with 0.1% Triton® X-100 (polyethylene glycol p-(1,1,3,3-tetramethylbutyl)-phenyl ether) is shown in the left panel (FIG. 3A) and treatment with a final concentration of 0.001% Triton® X-100 is shown in the right panel (FIG. 3B). Whole blood samples treated with Triton® X-100 data shown are representative of the other two detergents.

Detergent treated samples were analyzed using forward angle light scatter (FALS) versus side scatter (SS) to determine the relative integrity and separation of white blood cell populations. As shown in FIG. 3, treatment of fixed whole blood with 0.1% Triton® X-100 (polyethylene glycol p-(1,1,3,3-tetramethylbutyl)-phenyl ether) (left panel) showed distinct populations of lymphocytes, monocytes and granulocytes. In contrast, treatment with a final concentration of 0.001% Triton® X-100 showed no distinct WBC populations (right panel). Treatment of fixed samples with 0.01% Triton® X-100 showed similar lack of separation of WBC populations by light scatter (results not shown). Similar results were seen for three detergents that demonstrated significant red blood cell lysis (Triton® X-100, NP-40® and Brij 58®), with all three detergents showing similar patterns of RBC lysis and WBC population separation depending on the final detergent concentration (where only a specific final detergent concentration demonstrated clear separation of WBC populations, and other concentrations of the same detergent showed a no distinct separation).

For the three detergents that demonstrated RBC lysis (Triton® X-100 (polyethylene glycol p-(1,1,3,3-tetramethylbutyl)-phenyl ether), NP-40® and Brij 58®), the 0.1% final detergent concentration (of the three concentrations tested) showed separation of WBC populations by light scatter. For these three detergents, no RBC lysis was seen visibly at 0.01% and only partial lysis was seen visibly for samples treated with 0.001% detergent.

Figure 4:
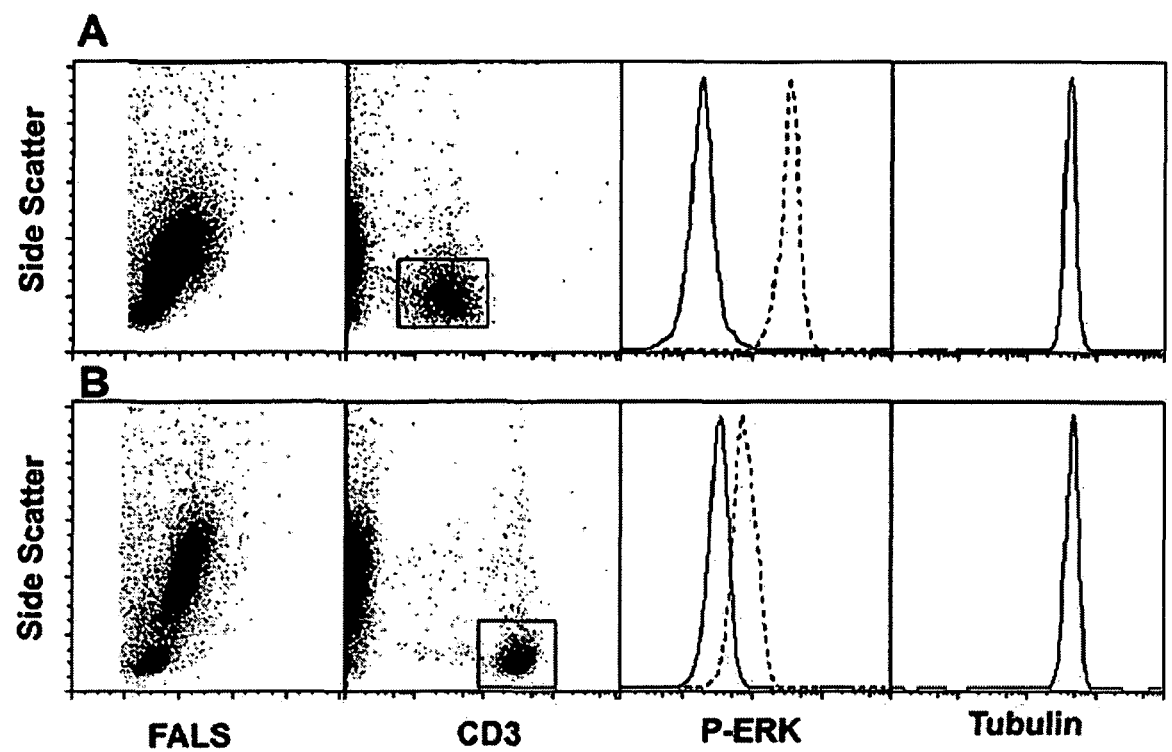
FIG. 4 shows a comparison of the results of whole blood samples prepared using Method A (hypotonic lysis technique)(top panels, FIG. 4A) versus 2% formaldehyde fixation followed by 0.1% Triton® X-100 (polyethylene glycol p-(1,1,3,3-tetramethylbutyl)-phenyl ether)(bottom panels, FIG. 4B). Typical results, shown here, demonstrate poor resolution of WBC populations by light scatter, lower intensity of CD3 staining but greater S/N for P-ERK from Method A. Similar anti-Tubulin staining intensity for both methods indicates similar accessibility of intracellular compartment for both methods.

Using formaldehyde fixation (2% at room temperature for 10 minutes) and 0.1% detergent treatment, phospho-ERK levels in PMA stimulated whole blood was only 2.5 to 3.5 times above unstimulated controls, as compared to 20 fold or higher levels in whole blood samples prepared using the hypotonic lysis method (Method A)(see FIG. 4).

As demonstrated in FIG. 4, cells prepared by the two different methods (Method A vs. formaldehyde/Triton (Method B)) and incubated with anti-tubulin-FITC showed identical percentage positive cells (essentially 100% of CD3 positive cells), and similar MFI for anti-Tubulin staining (FIG. 4, right panels), indicating equivalent access to intracellular antigens in cells prepared using either method and eliminating the possibility that the formaldehyde/detergent method does not provide sufficient cell permeabilization to allow antibody access to the cell interior.

The major differences in phospho-ERK, but not anti-tubulin, staining suggested that the phospho-ERK epitope, but not tubulin, requires unmasking or denaturation following cross linking fixation, a process provided by alcohol treatment in the hypotonic lysis (Method A) technique. However, as shown in FIGS. 2 and 4, alcohol treatment following formaldehyde fixation did not preserve light scatter characteristics and enable identification of all white cell populations. The formaldehyde/detergent technique, while preserving light scatter, did not unmask phospho-ERK.

Consequently, it was investigated whether the use of high salt, low pH and heat as denaturing conditions could potentially unmask phospho-ERK expression.

Antigen Unmasking Using High Salt, Low pH or Temperature

Following fixation of whole blood samples in 4% formaldehyde (10 minutes at room temperature) and treatment with 0.1% detergent for 30 minutes at room temperature (Triton® X-100 (polyethylene glycol p-(1,1,3,3-tetramethylbutyl)-phenyl ether), NP-40®, or Brij 58®), samples were made 1M or 2M in NaCl or Urea by the direct addition of concentrated stock solution (5M stock) to the detergent solution after visible RBC lysis. For samples exposed to low pH, detergent was removed by centrifugation (after 30 minute incubation) and cells were resuspended in PBS adjusted to pH 5. All samples were exposed to high salt or acid for 30 minutes at room temperature, centrifuged, and resuspended in wash buffer.

For samples exposed to increased temperature as a denaturating agent, fixed whole blood samples (4% formaldehyde for 10 minutes at room temperature) were treated with 0.1% Triton® X-100 (polyethylene glycol p-(1,1,3,3-tetramethylbutyl)-phenyl ether) for 30 minutes at room temperature, then incubated in a 70° C. water bath for 10 minutes, centrifuged, and resuspended in wash buffer. For all conditions, samples were stained with CD3-PE and phospho-ERK-Alexa 488, washed, and analyzed using an Epics Elite™.

Figure 5:
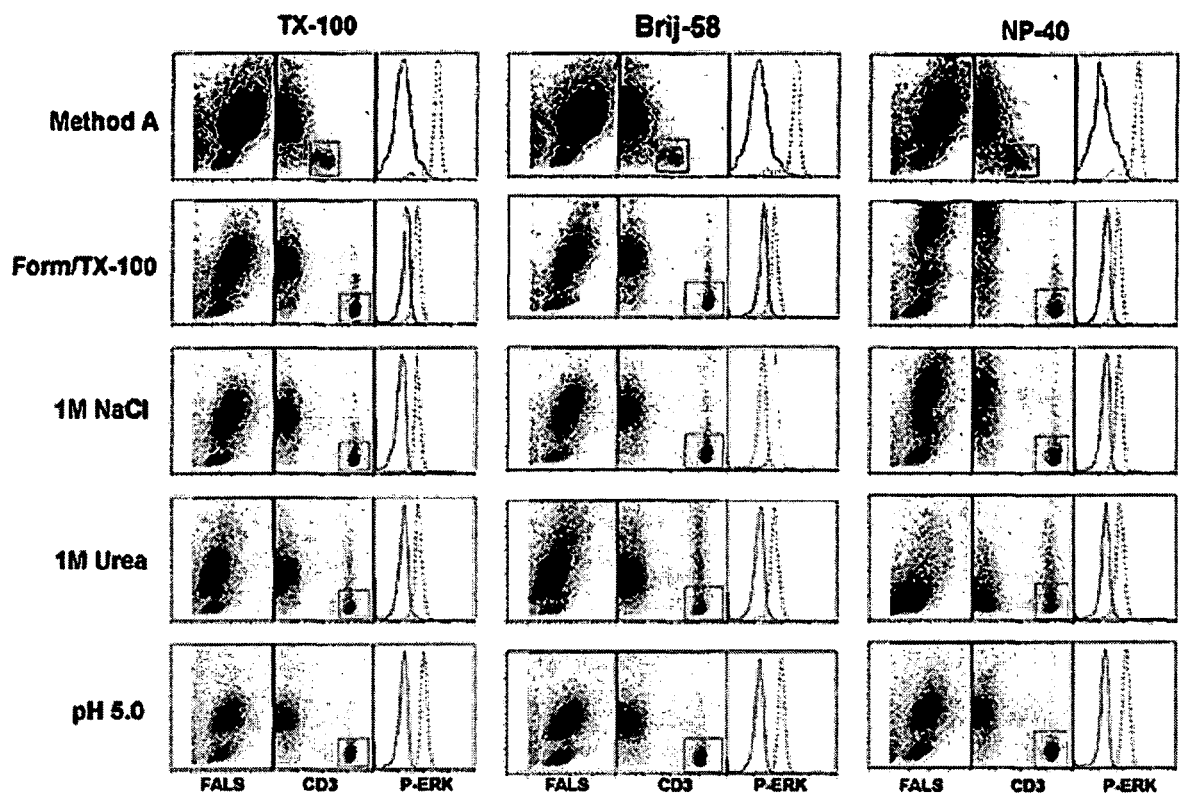
FIG. 5 shows the effect of different denaturing agents (rows) and different detergents (TX-100, right panels; Brij-58, center panels; NP-40, left panels) on light scatter measurements, CD3 expression, and P-ERK staining intensity.

The results, shown in FIG. 5 and summarized in Table 1, demonstrate that whole blood samples prepared by the hypotonic lysis technique (top row, FIG. 5) showed a 26 to 34 fold difference in phospho-ERK expression in CD3 positive lymphocytes, comparing stimulated to unstimulated samples. Samples treated with either 1 or 2N NaCl, or 1 or 2M Urea demonstrated small, but insignificant increases in phospho-ERK expression, compared to samples treated with detergent alone, while exposure to pH5 showed a 7 fold difference and 70 degrees Celsius treatment a 6 fold difference (PMA stimulated to unstimulated). Scatter patterns of (FALS vs SS) whole blood samples treated with any detergent and exposed to NaCL, Urea, or low pH showed poor resolution of white blood cell populations (FIG. 5, first row for each detergent treatment). The results shown are representative of identical experiments performed on three different whole blood samples.

TABLE 1

Impact of different denaturation conditions on p-ERK expression in CD3 positive lymphocytes[a]

| Denaturing Condition | MFI | | S/N |
|---|---|---|---|
| | Control | +PMA | |
| Method A[b] | 1.05 | 29.8 | 28.3 |
| Method B[c] | 1.71 | 4.9 | 2.9 |
| 1N NaCl | 1.65 | 5.6 | 3.4 |
| 2N NaCl | 1.03 | 4.98 | 4.8 |
| 1M Urea | 1.53 | 5.59 | 3.65 |
| 2M Urea | 1.38 | 5.86 | 4.2 |
| pH 5 | 1.47 | 10.58 | 7.19 |
| 70° C. | 1.54 | 9.83 | 6.38 |

[a]results shown are compiled from three individual experiments
[b]Method A- hypotonic lysis with fixation
[c]Method B- 4% formaldehyde/0.1% TX-100

These results, while indicating that denaturing conditions improved p-ERK expression in formaldehyde/detergent treated cells, the levels of expression were far less than those seen in whole blood samples treated by hypotonic RBC lysis, fixation, and alcohol treatment (Method A).

EXAMPLE II

Impact of Fixation Agent and Detergent Concentrations on White Blood Cell Light Scatter This example demonstrates the impact of concentration and incubation times for both fixative agent and detergent on the resolution and recovery of white blood cells.

Figure 6:
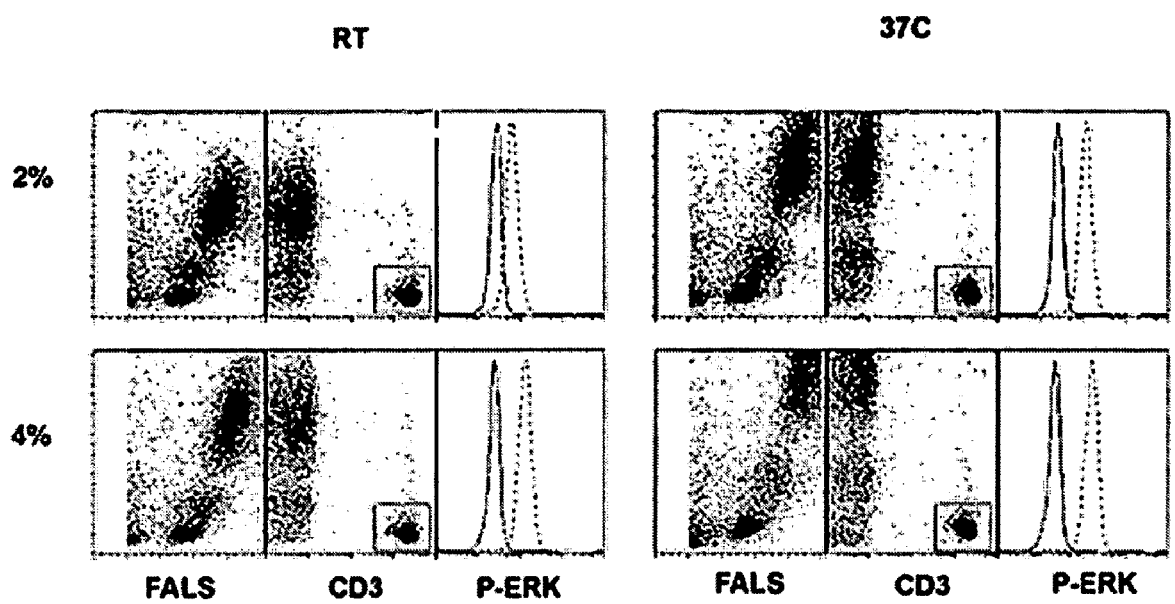
FIG. 6 shows the impact of different concentrations of Formaldehyde fixative and incubation temperatures on light scatter measurements, CD3 expression, and P-ERK staining intensity.

Based on previous studies that suggested that higher concentrations of cross linking fixative helps retain light scatter profiles and resolution of white blood cell populations, the impact of different fixative concentrations was investigated. Whole blood samples were fixed at room temperature or at 37 deg. C. for 10 minutes in increasing concentrations of formaldehyde (from 1% to 10% final concentration), then immediately incubated with 1 ml 0. 1% TX-100 (at room temperature). As shown in FIG. 6, increasing formaldehyde concentration from 2% to 4% (for room temperature incubation) significantly improved the resolution of white blood cell populations (left panels). Similarly, treatment of whole blood samples with formaldehyde at 37 deg C. resulted in improved separation of WBC populations using light scatter, without significant impact on CD3 expression (similar MFI's for both treatment temperatures, FIG. 6, center panels) However, higher concentrations of formaldehyde (greater than 4%) resulted in incomplete lysis of RBC's. and failure to resolve white blood cell populations (data not shown). As shown in FIG. 6 (right panels), treatment at 37 deg. C. also resulted in improved S/N for phospho-ERK expression (from 2.5 at room temperature, to 5.2 for 37 deg. C. treatment).

To determine the impact of detergent concentration on WBC recoveries, light scatter-based separation, and p-ERK expression, whole blood aliquots (100 ul) were fixed using 4% formaldehyde (final concentration) for 10 minutes at room temperature or at 37 deg C., and then incubated with 1 ml TX-100, using detergent concentrations from 0.1 to 1.0%. For these experiments, detergent was removed by centrifugation and washing (3× with wash buffer), and cells stained with anti-CD3-PE.

Figure 7:
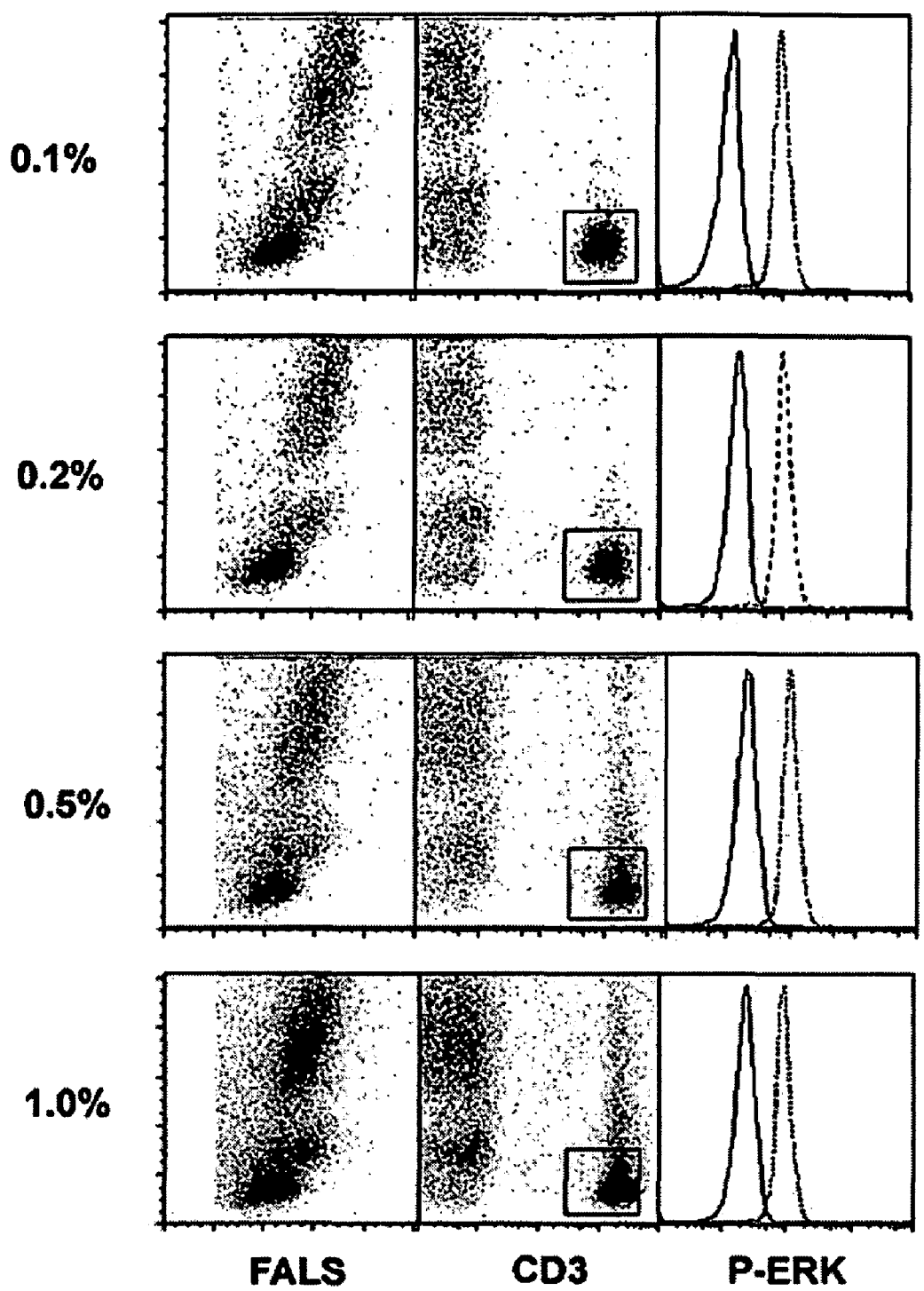
FIG. 7 shows the impact of different concentrations of Triton® X-100 (polyethylene glycol p-(1,1,3,3-tetramethylbutyl)-phenyl ether)(from 0.1% to 1.0%, top to bottom panels) on light scatter measurements, CD3 expression, and P-ERK staining intensity.

As shown in FIG. 7, increasing detergent concentration above 0.1% resulted in poorer resolution of WBC populations, with increasing amounts of debris, and significant loss of resolution of monocytes from lymphocytes using light scatter (see FIG. 7 left panels). In addition, with the use of increasing detergent concentrations, the CD3 versus side scatter histograms (FIG. 7 center panels) showed increasing percentages of CD3 positive events with side scatter profiles significantly higher than found in lymphocytes. As shown in FIG. 7, fixation at room temperature resulted in RBC lysis with all concentrations of detergent, while samples fixed at 37 deg C. demonstrated cell clumping and incomplete RBC lysis at all detergent concentrations.

These results suggest that with increasing detergent concentration, either CD3 positive lymphocytes are binding to monocytes or granulocytes, or that lysed CD3 positive lymphocytes are binding membrane fragments to monocytes and granulocytes (later more consistent with SS profiles seen in center panels in FIG. 7). Together with the data on titration of fixative, these data indicate that optimal RBC lysis and WBC recoveries are obtained using 4% formaldehyde and 0.1% TX-100 treatment. However, studies with p-ERK staining of cells treated with the range of formaldehyde and TX-100 discussed above failed to provide a p-ERK signal (for PMA stimulated whole blood samples) greater than 7.4 times higher than unstimulated control samples (compared to ~28 fold for the hypotonic lysis treatment originally described).

The effect of incubation time of whole blood samples with fixative was next investigated, using 4% formaldehyde (10 to 30 minutes). In addition, the effect of incubating the sample (after addition of fixative) with detergent either in the presence of fixative (as previously described), or after the removal of fixative was investigated. Samples incubated in fixative for periods greater than 10 minutes showed incomplete RBC lysis and cell clumping (results not shown). Samples treated with detergent in the presence of fixative showed more complete RBC lysis and better resolution of white blood cell populations, compared to samples incubated with fixative for 10 minutes, washed, then treated with detergent (for periods of 10 to 30 minutes)(results not shown). At this point, although whole blood samples showed good RBC lysis and good resolution of lymphocytes, monocytes, and granulocytes, the signal to noise ratio for phospho-ERK1/2 remained at 5-8, indicating significant masking of this intracellular antigen epitope still existed.

EXAMPLE III

Impact of Alcohol Unmasking Agent on P-ERK and Impact on CD3 Expression

This example demonstrates the impact of alcohol on lymphocyte recovery and unmasking of surface epitopes.

In order to "unmask" phospho-protein (and other) epitopes rendered unreactive following fixation with cross linking fixatives, a series of experiments was undertaken to evaluate the impact of alcohol treatment following detergent treatment. Following 30 minute exposure to detergent, fixed whole blood samples were washed with cold (4 deg C.) buffer (PBS w/o Ca++ or Mg++) and resuspended in a series of different concentrations of methanol or ethanol at 4 deg C. One aliquot of each sample was held overnight at 4 deg. C. to investigate the impact of storage in alcohol solutions. As before, samples were stained (following removal of alcohol by centrifugation and washing in PBS) with antibodies to CD3-PE (to evaluate T-lymphocyte recovery and staining) and phospho-ERK (to evaluate epitope unmasking).

Figure 8:
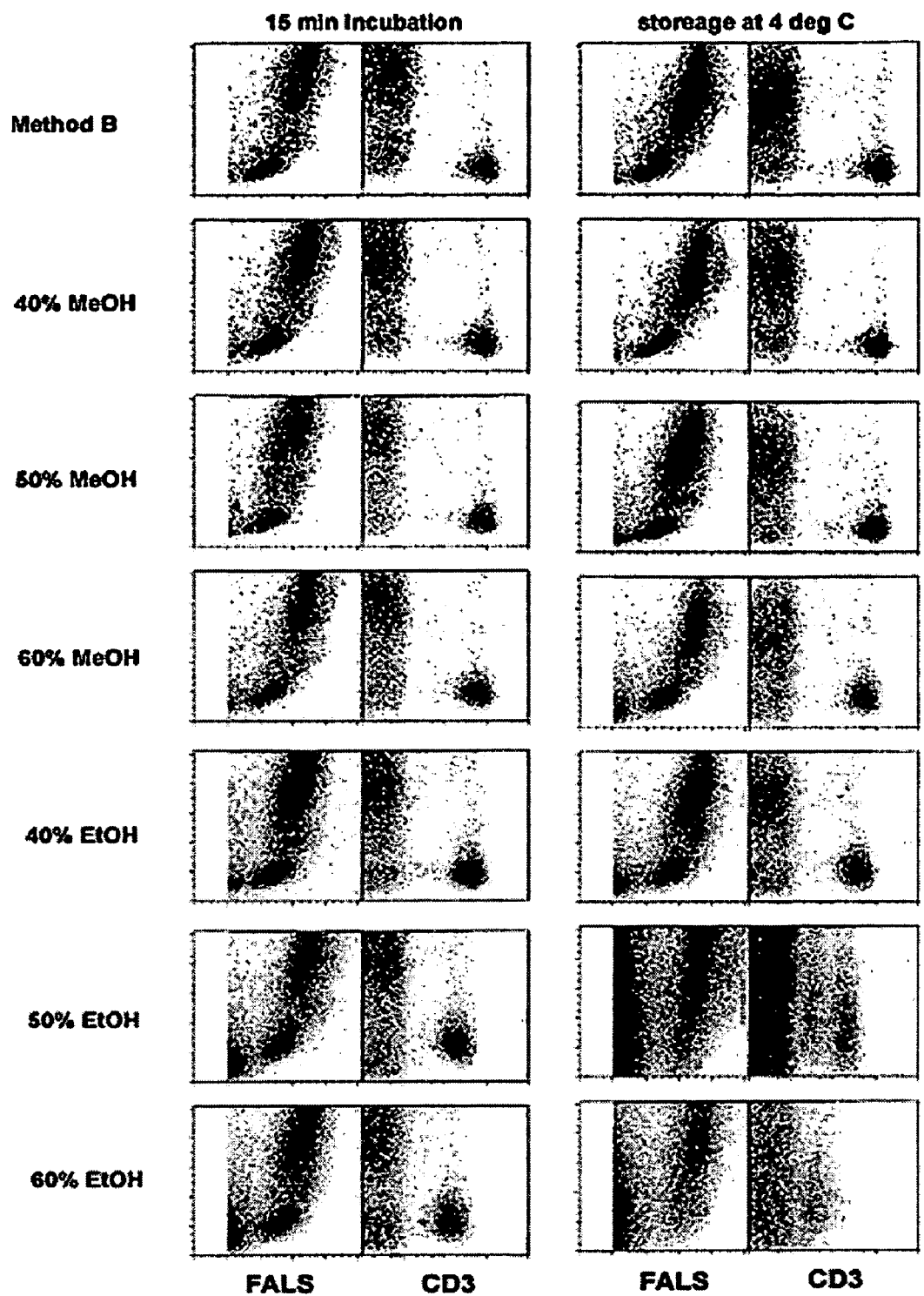
FIG. 8 shows the effects of different alcohol concentrations (methanol or ethanol) used for "unmasking" on light scatter measurements and on CD3 expression. Paired samples were incubated at each alcohol concentration for 15 min, or overnight storage at 4 deg. C. before CD3 staining.

As shown in results presented in FIG. 8, methanol treatment (from 40 to 60% final concentration) preserved WBC light scatter profiles while retaining good CD3 staining. Ethanol treatment resulted in a higher percentage of debris (FIG. 8, lower left panels) as well as a loss of monocytes. Since many labs routinely hold samples in alcohol at 4 deg C. for variable periods of time, as part of these studies, we held duplicate samples overnight in alcohol solutions before analysis. The results, shown in FIG. 8 (right panels) demonstrate that while there is some increase in percentage of debris in solutions held overnight in methanol, there were no significant deterioration in either the light scatter or in CD3 expression in methanol treated samples. In contrast, samples held overnight in ethanol (FIG. 8, lower right panels) showed significant debris, deterioration in light scatter and loss of CD3 staining.

EXAMPLE IV

Impact of Alcohol Treatment on White Blood Cell Populations

This example describes the impact of alcohol treatment on scatter separation of lymphocyte populations.

Examples I through III above describe two methods for whole blood samples to fix, lyse RBC's, and permeabilize cells for intracellular antigen staining for flow cytometry. In one embodiment of the basic method referred to as the fixation/detergent lysis technique, whole blood samples can be fixed using 4% formaldehyde for 10 min at room temperature, followed by the addition of 1 ml 0.1% Triton® X-100 (polyethylene glycol p-(1,1,3,3-tetramethylbutyl)-phenyl ether) at room temperature, without the removal of fixative (Method B). Further treatment with cold (4 ° C.) 50% methanol (in distilled water or buffer) can be employed to unmask protein epitopes requiring a denaturation step (Method B').

Figure 9:
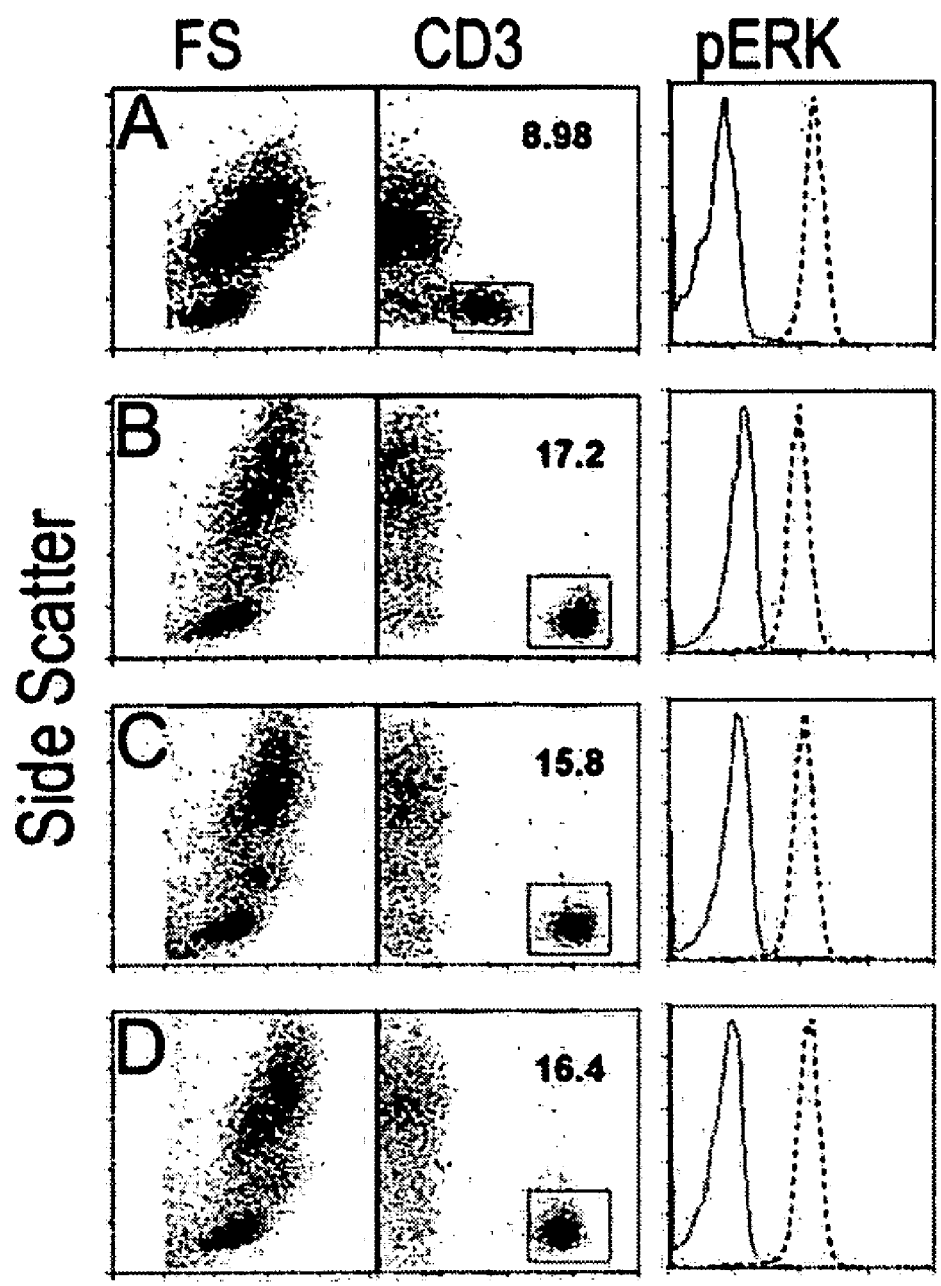
FIG. 9 shows a comparison of the effects of different cell preparation methods, showing the impact of whole blood lysis (top rows), Method B (middle rows), or Method B' (bottom rows) on light scatter measurements, CD3 expression, and P-ERK levels.

As shown in FIG. 9, treatment of whole blood samples by Method B resulted in good light scatter separation of WBC populations, high levels of CD3 expression on T-lymphocytes, but lower levels of p-ERK expression (FIG. 9 second set of panels) compared to whole blood treated with our original hypotonic lysis technique (Method A, FIG. 9, top set of panels). Whole blood samples treated with 50% methanol after detergent treatment (Method B', FIG. 9 third set of panels) retained WBC light scatter properties, CD3 expression and relatively high levels of p-ERK (here S/N=19.1 for Method B', S/N=8.1 for Method B, and S/N=29 for Method A).

In order to determine the impact of the two techniques (Method B and B') on the resolution of white blood cell populations, a series of experiments was performed comparing whole blood samples treated using the Q-Prep™ system (Beckman Coulter, Inc.), or the fixation/detergent lysis technique (Method B), or fixation/detergent lysis followed by 50% cold methanol (Method B').

Samples from individual normal donors were treated using these three different techniques, and measured by flow cytometry (using FALS vs SS) to determine the relative separation of lymphocytes, monocytes and granulocytes using measurements of the Fisher distances between light scatter populations as described by Riley Statistical analysis and optimal classification of blood cell populations using Gaussian distributions, Ph.D. dissertation: Florida International University; (2003).

Briefly, to determine the relative effect of different whole blood preparation techniques on the recovery and identification of the major white blood cell populations (lymphocytes, monocytes, and granulocytes), experiments were performed comparing the separation of these three populations by forward versus 90 degree light scatter parameters (both linear), using a measurement of Fisher Distances as described by Riley, supra, 2003.

As illustrated in FIG. 1, this technique measures the center of mass of each light scatter-based population along the two major axes (X and Y), and calculates the hypotenuse of the right triangle where $C=\sqrt{A^2+B^2}$. The Fisher Distance between lymphocytes (A) and monocytes $$(B) = \frac{C}{SD(A) + SD(B)}$$

where SD=Standard Deviation. Each population was calculated by adding the SD of each population along the X plus the Y axes and dividing by two. While this calculation does not provide the true population SD, it does provide a valid and useful approximation that can be readily calculated. In order to calculate Fisher Distances, samples prepared by each of the three techniques were analyzed on a single FC-500™ flow cytometer, counting a total of 45,000 events, as noted above. For samples prepared using Q-Prep™ or Method B without alcohol, identical settings for gain and high voltage were used for both FALS and side-scatter detectors. For samples prepared using alcohol treatment (Method B') a higher voltage was used for both scatter detectors (3.3 times higher for both voltages) to enable resolution of the three populations.

Lymphocyte, monocyte and granulocyte enumerations were obtained using FALS and side-scatter to calculate percentage distributions for individual samples. Individual values (percent) were multiplied by the WBC count obtained on that donor, using the CBC (obtained from LH-750™). To assess test precision (reproducibility), means, standard deviations, and coefficients of variation were calculated for each set of replicates (tubes stained with CD45, 3, 19, 13, 14, and 33).

Methods of sample preparations were compared for Fisher distances, CBC parameters, and MFI's of surface markers. Analysis of variance and Tukey-Kramer tests were used for comparing methods for Fisher distances. Methods were compared in terms of differences and total bias for individual CD's using MFI, and for CBC parameters using difference plots, as described by Bland and Altman, Lancet 1:307-31 (1986). Differences between two methods for each blood specimen can be statistically modeled as, $$D=TB+E$$

where D is the difference, TB is total bias, and E is a random error. Since E is mostly associated with imprecision, the value of its standard deviation is also an estimate of the imprecision of the assay. Details on the estimation of TB can be found in Magari Journal of Biopharmaceutical Statistics, 2004 (in press). Tolerance limits for 95% confidence and 99% coverage are calculated based on the estimates of standard error. SAS (SAS Institute Inc., Carry, N.C.) was used for all statistical analyses.

The results of measurements of 24 normal donors comparing all three techniques are summarized in Table 2. Fisher Distances between lymphocytes and monocytes were greatest for samples prepared using Q-Prep™ (Fisher Distance=2.19), indicating this technique had the best separation of monocytes from lymphocytes (and for separation of monocytes from granulocytes) for the three techniques tested. The analysis demonstrated a significant difference comparing Fisher Distances of samples prepared using Q-Prep™ and Method B. However, there was no significant difference comparing Fisher Distances from lymphocytes to monocytes for Method B versus Method B'. Since each sample was stained with six different CD markers, we also analyzed the sample variability within samples, as well as between techniques. This analysis demonstrated a greater intra-assay variability as compared to the variability between samples prepared with the same technique.

In comparing the Fisher Distances between monocytes and granulocytes (Table 2), all three techniques gave significantly different results, with Q-Prep™ demonstrating the best separation, followed by Method B. While our overall analysis indicates that Method B and B' provide separation of WBC populations that are not as good as those provided by Q-Prep™, scatter measurements (FALS and SS) for whole blood samples prepared using Method B or B' provide sufficient resolution to clearly resolve WBC populations, and generally provide significantly better resolution than provided by our original hypotonic lysis technique (see top panel, FIG. 9).

TABLE 2

Summary of Data Analysis for Fisher Distance Calculations

| Method | Fisher Distance | SE | DF | t-value | p-value |
| --- | --- | --- | --- | --- | --- |
| Lymphocytes to Monocytes | | | | | |
| Q-Prep | 2.1994 | 0.02687 | 408 | 81.86 | <.0001 |
| Method B | 1.7644 | 0.02687 | 408 | 65.67 | <.0001 |
| Method B' (w MeOH) | 1.7441 | 0.02687 | 408 | 64.92 | <.0001 |

TABLE 2-continued

Summary of Data Analysis for Fisher Distance Calculations

| Method | Fisher Distance | SE | DF | t-value | p-value |
| --- | --- | --- | --- | --- | --- |
| Monocytes to Granulocytes | | | | | |
| Q-Prep | 2.5735 | 0.04362 | 408 | 59 | <.0001 |
| Method B | 2.1733 | 0.04362 | 408 | 49.82 | <.0001 |
| Method B' (w MeOH) | 1.9682 | 0.04362 | 408 | 45.12 | <.0001 |

Figure 10:
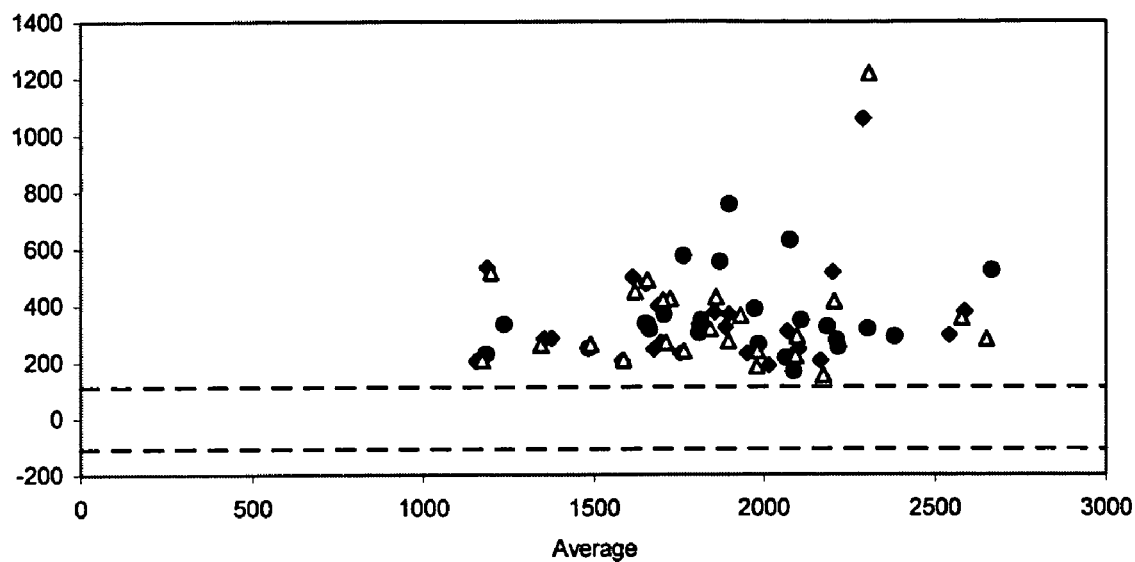
FIG. 10 shows Total Bias plots for different WBC populations (lymphocytes, monocytes, and granulocytes) as determined by flow cytometric light scatter measurements of whole blood samples prepared by three different techniques (Q-Prep™, Method B, or Method B"). Values for three different techniques were compared to differential counts obtained using an LH-750™ differential cell count on each sample.
Figure 10:
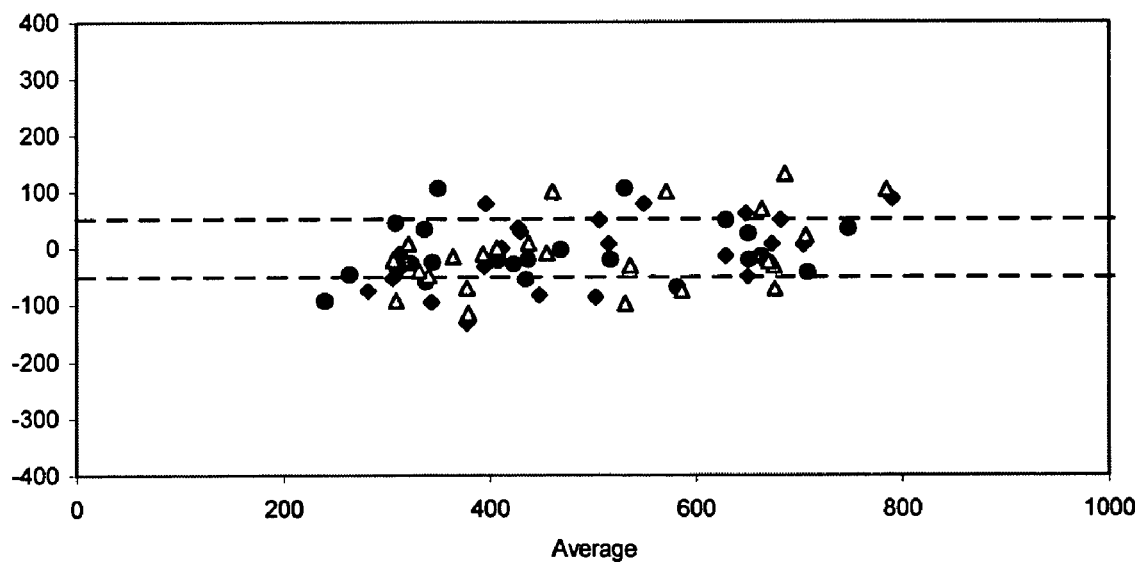
Figure 10:
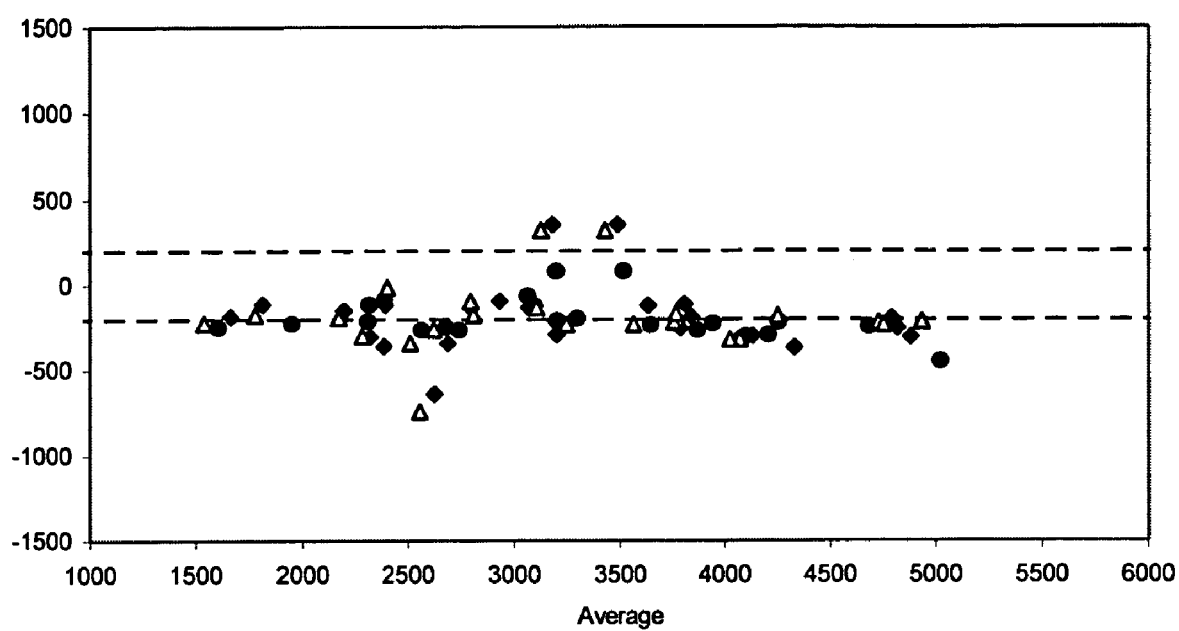

Aliquots of whole blood samples prepared by all three techniques were measured using an LH-750™ (Beckman Coulter, Inc.) analyzer to obtain lymphocyte, monocyte and granulocytes counts (CBC) in order to determine if any blood cell population was decreased (lost) as a consequence of sample preparation (previous experiments using lower fixation concentration, plus detergent and alcohol treatments had indicated a significant and preferential loss of monocytes). Analysis was performed using bias plots (FIG. 10) to determine if there was a significant difference in recoveries of different WBC populations. Lymphocyte populations (FIG. 10, top panel) were consistently overestimated for all three whole blood preparation techniques as compared with the CBC determination, with no significant difference in lymphocyte determinations when comparing the three whole blood techniques. This difference between the three flow cytometric lymphocyte determinations and the CBC can be explained as the result of including events with low scatter (debris, platelets) in the lymphocyte gate. Comparisons of the recoveries of monocytes (FIG. 10, center panel) and granulocytes (FIG. 10, bottom panel) showed no significant variations for any of the whole blood techniques for monocytes, and a small but insignificant decrease in the recoveries of granulocytes for all three whole blood techniques compared with the CBC.

EXAMPLE V

Impact of Whole Blood Fixation Techniques on Representative CD Marker Expression This example demonstrates the impact of various fixation, RBC lysis, and permeabilization techniques, either with or without the addition of 50% cold methanol, on a representative set of cell surface markers.

A final set of experiments investigated the impact of the fixation, RBC lysis, and permeabilization techniques (with or without the addition of 50% cold methanol) on cell surface markers for lymphocytes (CD3, 19), monocytes (CD13, 14), and granulocytes (CD13, 33)). As previously described, whole blood samples were prepared using Q-Prep® or fixation/detergent lysis with or without alcohol. After washing, samples were incubated with a single antibody (all as PE conjugates), and analyzed by flow cytometry to determine the percent positive cells and the mean fluorescence intensity (MFI).

Figure 11:
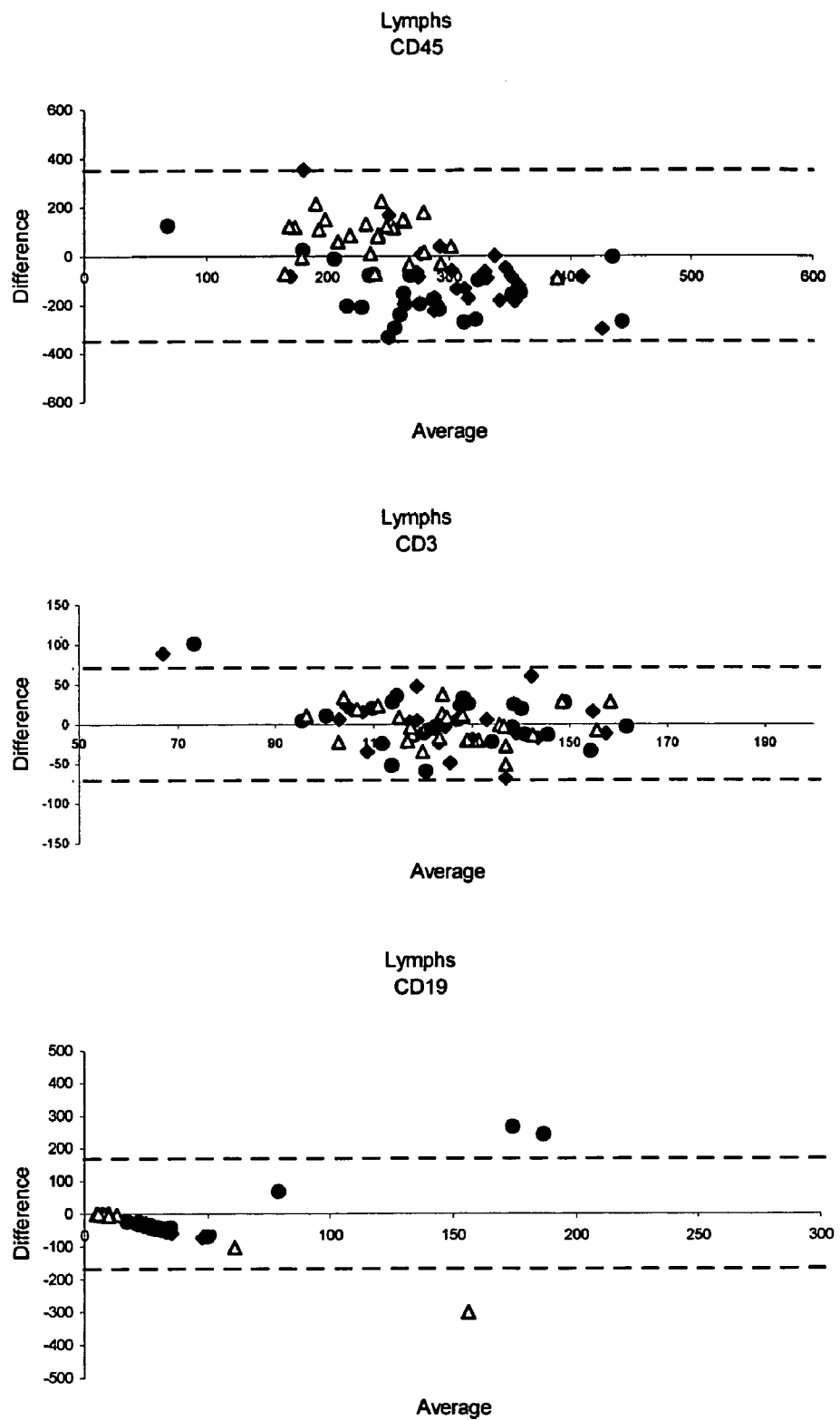
FIG. 11 shows estimates of Total Bias based on measurements of MFI (mean fluorescence intensity) for different WBC populations (lymphocytes, monocytes, and granulocytes) for whole blood samples prepared by three different techniques (Q-Prep, Method B ("Abbrev"), or Method B' ("Full"). Approximate tolerance limits are plotted against the average between the two methods for enumerating WBC populations for each of the six different CD markers used.
Figure 11:
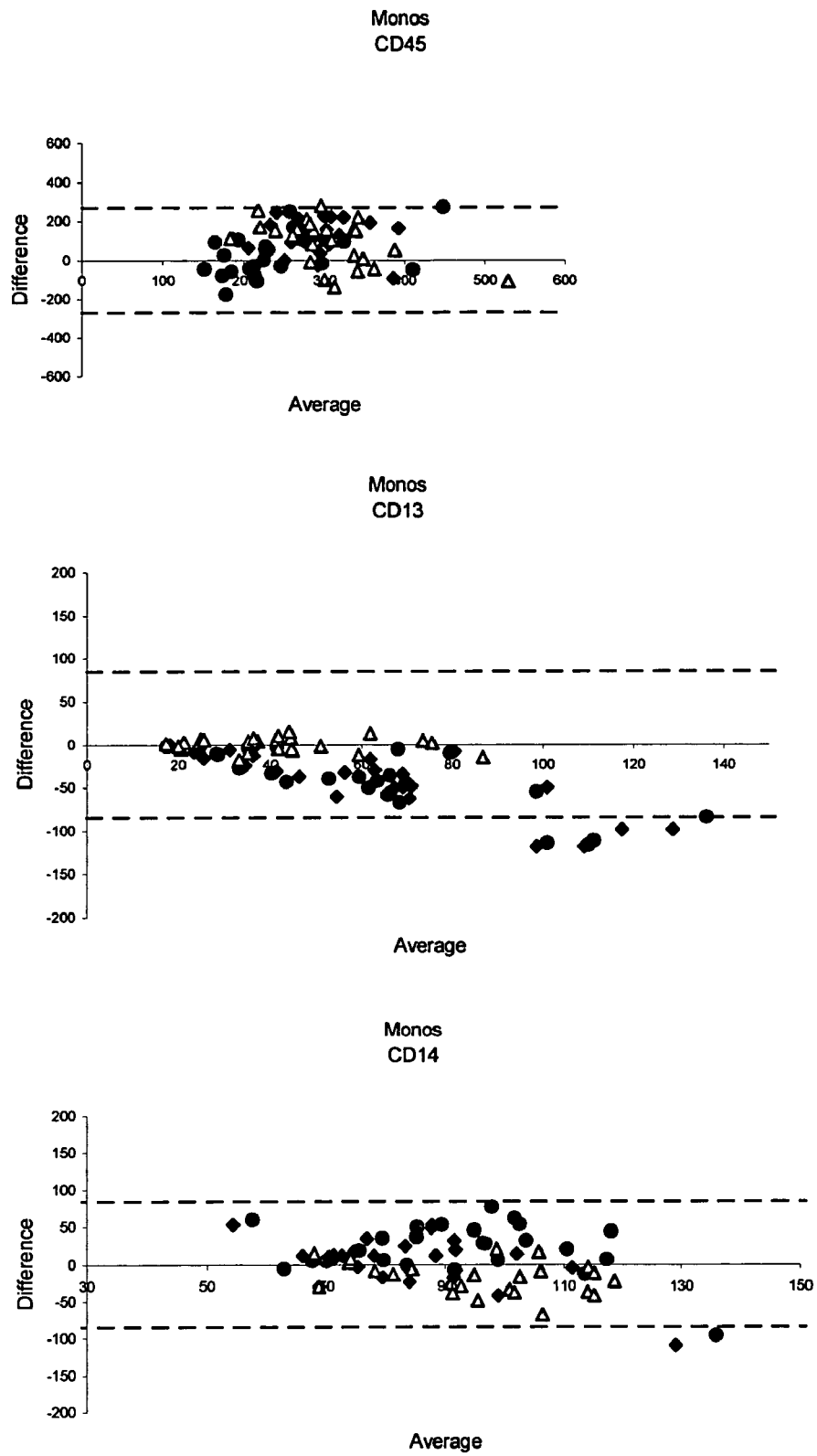
Figure 11:
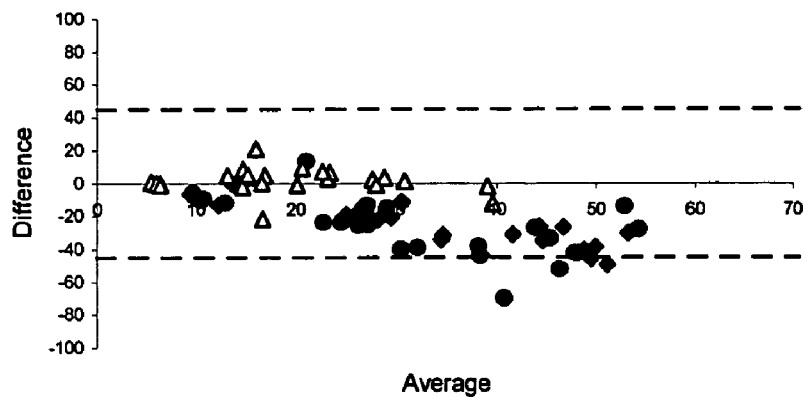
Figure 11:
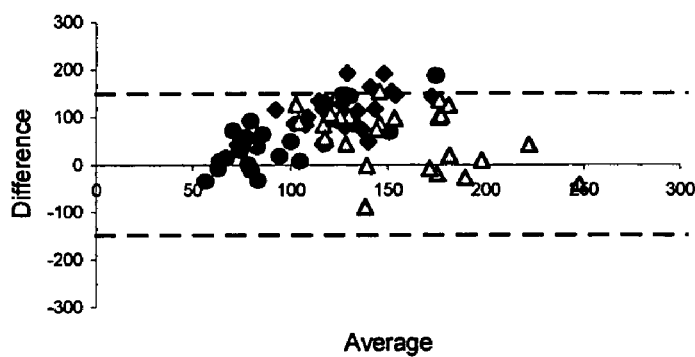
Figure 11:
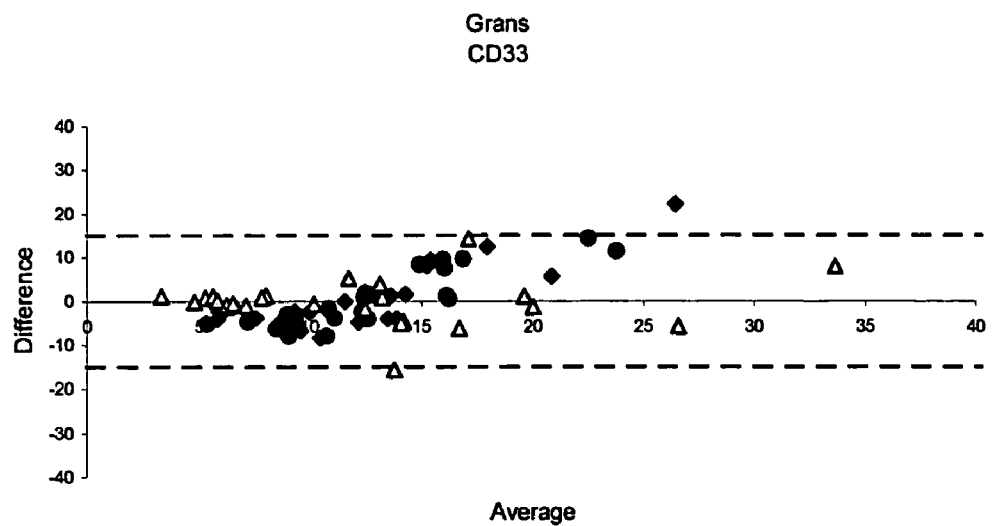
Figure 11:
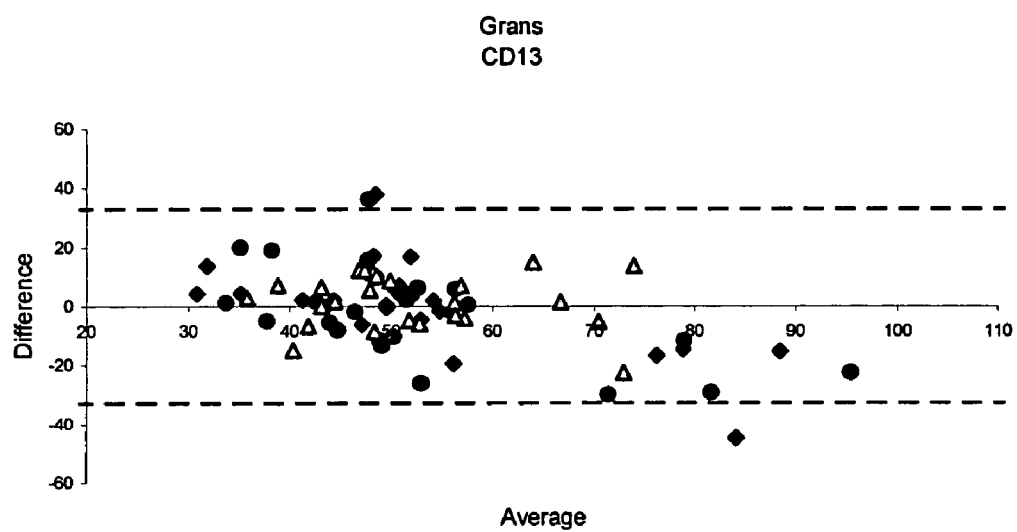

The results of CD marker determinations on 24 individual donors are presented in Table 3 and FIG. 11. As shown in Table 3, while there was some variation in the MFI for any one marker in comparing the three different whole blood preparation techniques, the only significant decrease in staining intensity was seen for CD19 in whole blood samples treated with 50% methanol (Method B').

As shown in the bias plot for CD 19 expression (FIG. 11, third panel), there was considerable variability for expression of this marker in samples prepared using Method B or B', suggesting differential sensitivity of this epitope to formaldehyde/Triton (and methanol) treatment in individual blood donors. CD 19 positive cells could be readily detected in all donors, irregardless of the whole blood preparation technique used. While other markers showed some increase or decrease in staining intensity (MFI) in comparing different methods, in all cases there was sufficient staining intensity to readily identify positive versus negative cell populations for these six representative CD markers.

TABLE 3

Intensity of CD Marker Expression on Different WBC Populations using Different Whole Blood Preparation Techniques

| | Mean Fluorescence Intensity (MFI) | | | | | |
|---|---|---|---|---|---|---|
| | Q-Prep ™ | | Method B F/TX (no MeOH) | | Method B' (F/TX w MeOH) | |
| Marker | Mean | SD | Mean | SD | Mean | SD |
| Lymphocytes[a] | | | | | | |
| CD45 | 353.6 | 110.7 | 201.7 | 76.0 | 275.6 | 56.9 |
| CD3 | 123.1 | 29.7 | 126.6 | 20.5 | 124.9 | 18.7 |
| CD19 | 48.3 | 12.0 | 36.6 | 84.2 | 6.3[b] | 1.9 |
| Monocytes[a] | | | | | | |
| CD45 | 224.9 | 66.8 | 260 | 108.8 | 351.3 | 62.7 |
| CD13 | 84.1 | 45.6 | 41.5 | 19.2 | 41.9 | 18.3 |
| CD14 | 81.4 | 28.9 | 103.7 | 21.6 | 86.4 | 15.7 |
| CD33 | 44.0 | 20.9 | 18.9 | 10.7 | 20.1 | 9.4 |
| Granulocytes[a] | | | | | | |
| CD45 | 69.9 | 20.9 | 127.0 | 56.9 | 185.7 | 37.8 |
| CD13 | 53.3 | 20.5 | 51.4 | 12.0 | 53.0 | 6.0 |
| CD33 | 12.1 | 2.7 | 12.2 | 7.6 | 12.0 | 7.9 |

[a]WBC populations determined by light scatter (FALS versus SS)
[b]Significant decrease in level of CD expression compared with Q-Prep ™

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method of preparing a biological sample containing red blood cells and white blood cells for measurement of protein epitopes, said method allowing for the preservation of intracellular protein epitopes for detection, said method comprising the steps of:
   (a) a fixation step comprising contacting a biological sample containing red blood cells and white blood cells with a fixative, wherein said fixative is added in an amount to achieve a final concentration sufficient to crosslink proteins, lipoproteins and nucleic acid molecules;
   (b) a detergent step comprising contacting said sample from step (a) with a detergent, wherein said detergent is added in an amount to achieve a final concentration sufficient to lyse said red blood cells and permeabilize said white blood cells;
   (c) a detergent removal step comprising removing said detergent from said sample;
   (d) an alcohol step comprising contacting said sample with an alcohol in an amount to achieve a final concentration, which is sufficient to unmask said intracellular epitopes that have been made inaccessible by the fixative without reducing the reactivity of cell surface epitopes, wherein the alcohol step is performed after the detergent step, after the detergent removal step, or together with the detergent step; and,
   (e) a labeling step comprising contacting said sample with a detectable binding agent specific for one or more protein epitopes after the detergent removal step and the alcohol step.

2. The method of claim 1, wherein the detergent removal step comprises centrifuging said sample.

3. A method for preparing a biological sample containing red blood cells and white blood cells for measurement of protein epitopes, said method allowing for the preservation of intracellular protein epitopes for detection, said method comprising the steps of:
   (a) a fixation step comprising contacting a biological sample containing red blood cells and white blood cells with a fixative, wherein said fixative is added in an amount to achieve a final concentration sufficient to crosslink proteins, lipoproteins and nucleic acid molecules;
   (b) a detergent step comprising contacting said sample, from step (a) with a detergent, wherein said detergent is added in an amount to achieve a final concentration sufficient to lyse said red blood cells and permeabilize said white blood cells;
   (c) an alcohol step comprising contacting said sample with an alcohol in an amount to achieve a final concentration above which is sufficient to unmask said intracellular protein epitopes that have been made inaccessible by the fixative without reducing the reactivity of cell surface epitopes, wherein the alcohol step is performed after the detergent step or together with the detergent step; and,
   (d) a labeling step comprising contacting said sample from step (c) with a detectable binding agent specific for one or more protein epitopes.

4. The method of claim 3, wherein said alcohol concentration is between approximately 25 percent and approximately 75 percent.

5. The method of claim 3, wherein said alcohol is selected from the group consisting of ethanol and methanol.

6. The method of claim 3, wherein said alcohol is methanol.

7. The method of claim 3, wherein steps (a) and (b) are performed at room temperature.

8. The method of claim 3, wherein steps (a) and (b) are performed at 37 degrees Celsius.

9. The method of claim 3, wherein said sample can be stored at temperatures below freezing point without diminishing accessibility of said intracellular protein epitopes.

10. The method of claim 9, wherein said temperature is approximately −20 degrees Celsius.

11. The method of claim 3, further comprising an initial step comprising activating the sample with phorbol myristate acetate (PMA) activation of T-lymphocytes.

12. The method of claim 3, wherein said intracellular protein epitopes comprise phosphorylated epitopes.

13. The method of claim 12, wherein said intracellular proteins are involved in signal transduction pathways.

14. The method of claim 3, wherein said detection is accomplished by cytometry.

15. The method of claim 14, wherein said cytometry is flow cytometry.

16. The method of claim 14, wherein said cytometry is laser scanning cytometry.

17. The method of claim 14, wherein said cytometry is image cytometry.

18. The method of claim 3, further comprising an incubation step comprising incubating said sample subsequent to step (a) and prior to step (b).

19. The method of claim 18, wherein said incubation step is for a time period ranging between approximately 30 seconds and approximately one hour.

20. The method of claim 3, further comprising an incubation step comprising incubating said sample subsequent to step (b) and prior to step (c).

21. The method of claim 20, wherein said incubation step is for a time period ranging between approximately 30 seconds and approximately 1 hour.

22. The method of claim 21, wherein said time period is approximately 10 minutes.

23. The method of claim 3, wherein said fixative concentration is between approximately 0.1 percent and approximately twenty percent.

24. The method of claim 23, wherein said fixative concentration is between approximately 1 percent and approximately 4 percent.

25. The method of claim 3, wherein said fixative is formaldehyde.

26. The method of claim 3, wherein said detergent concentration is between approximately 0.1 percent and approximately 8 percent.

27. The method of claim 26, wherein said detergent concentration is between approximately 0.1 percent and approximately 1 percent.

28. The method of claim 3, wherein said detergent is an ionic detergent.

29. The method of claim 28, wherein said ionic detergent is selected from the group consisting of Nonidet® P-40 (NP-40, octylphenolpoly (ethyleneglycolether)) and Brij-58® (poly (oxyethylene) cetyl ether).

30. The method of claim 3, further comprising a centrifugation step comprising centrifuging said sample subsequent to step (b) and prior to step (c).

31. The method of claim 3, further comprising a centrifugation step comprising centrifuging said sample subsequent to step (c).

32. The method of claim 3, wherein said biological sample is selected from the group consisting of blood, bone marrow aspirate and peritoneal fluid.

33. The method of claim 32, wherein said biological sample comprises undiluted peripheral blood.

34. The method of claim 3, wherein said alcohol concentration is above approximately 40 percent.

35. The method of claim 3, wherein said alcohol concentration is between approximately 40 percent and approximately 60 percent.

36. The method of claim 3, wherein said detergent is a non-ionic detergent.

37. The method of claim 36, wherein said non-ionic detergent is Triton-X-100 (polyethylene glycol p-(1,1,3,3-tetramethylbutyl)-phenyl ether).

* * * * *